(12) United States Patent
Herrmann et al.

(10) Patent No.: US 7,176,011 B2
(45) Date of Patent: Feb. 13, 2007

(54) LIPID CLEAVAGE ENZYME

(75) Inventors: Dieter Herrmann, Heidelberg (DE);
Hans-George Opitz, Weinheim (DE);
Harald Zilch, Mannheim (DE)

(73) Assignee: Heidelberg Pharma AG, Heidelberg (DE)

( * ) Notice: Subject to any disclaimer, the term of this patent is extended or adjusted under 35 U.S.C. 154(b) by 526 days.

(21) Appl. No.: 10/211,260

(22) Filed: Aug. 5, 2002

(65) Prior Publication Data

US 2003/0082167 A1    May 1, 2003

Related U.S. Application Data

(63) Continuation of application No. 09/472,184, filed on Dec. 27, 1999, now abandoned, which is a continuation of application No. 09/232,732, filed on Jan. 19, 1999, now abandoned, which is a continuation of application No. 08/836,046, filed on Jul. 8, 1997, now abandoned.

(30) Foreign Application Priority Data

Nov. 12, 1994 (DE) ................................. 44 40 472
May 18, 1995 (DE) ................................ 195 18 278

(51) Int. Cl.
*C12N 9/20* (2006.01)
*C12N 9/18* (2006.01)
(52) U.S. Cl. ....................... 435/198; 435/197
(58) Field of Classification Search ................ 435/197, 435/198
See application file for complete search history.

(56) References Cited

U.S. PATENT DOCUMENTS 5,512,671 A * 4/1996 Piantadosi et al.
6,077,837 A * 6/2000 Kozak

FOREIGN PATENT DOCUMENTS

WO    WO 9119726 A1 * 12/1991

OTHER PUBLICATIONS

Warren et al. "Three-peaked chemiluminescent response of human peripheral blood leukocytes following stimulations with phytohaemagglutinin (PHA)," J. Biolum. Chemilum. (1990) 5: 235-241.*
Record et al. "A rapid isolation procedure of plasma membranes from human neutrophils using self-generating Percoll gradients. Importance of pH in avoiding contamination by intracellular membranes" Biochim. Biophys. Acta (1985) 819: 1-9.*
Hostetler et al., "Synthesis and Antiretroviral Activity of Phospholipid Analogs of Azidothymidine and Other Antiviral Nucleosides" (1990) J. Biol. Chem., 265(11), 6112-6117.*
Piantadosi et al., "Synthesis and Evaluation of Novel Ether Lipid Nucleoside Conjugates for Anti-HIV Activity" (1991) J. Med. Chem., 34(4), 1408-1414.*
Davitz et al., "Purification of a Glycosyl-phospatidylinositol-specific Phospholipase D from Human Plasma" (1989) J. Biol. Chem., 264(23), 13760-13764.*

* cited by examiner

*Primary Examiner*—Leon B. Lankford, Jr.
*Assistant Examiner*—Susan Hanley
(74) *Attorney, Agent, or Firm*—Rothwell, Figg, Ernst & Manbeck

(57) ABSTRACT

A membranous enzyme not yet described in the state-of-the-art can be extracted from cellular membrane fractions of blood leukocytes or monocytes/macrophages. Also disclosed is the use of substrates of this enzyme to prepare medicaments that contain these substrates as pharmaceutical active substance. These medicaments are useful to direct pharmacologically active substances to target cells and to enrich target cells with said substances. Also disclosed are in-vitro research systems containing this enzyme used to detect other substrates of this enzyme.

16 Claims, 18 Drawing Sheets

LIPID CLEAVAGE ENZYME

Figure 1:
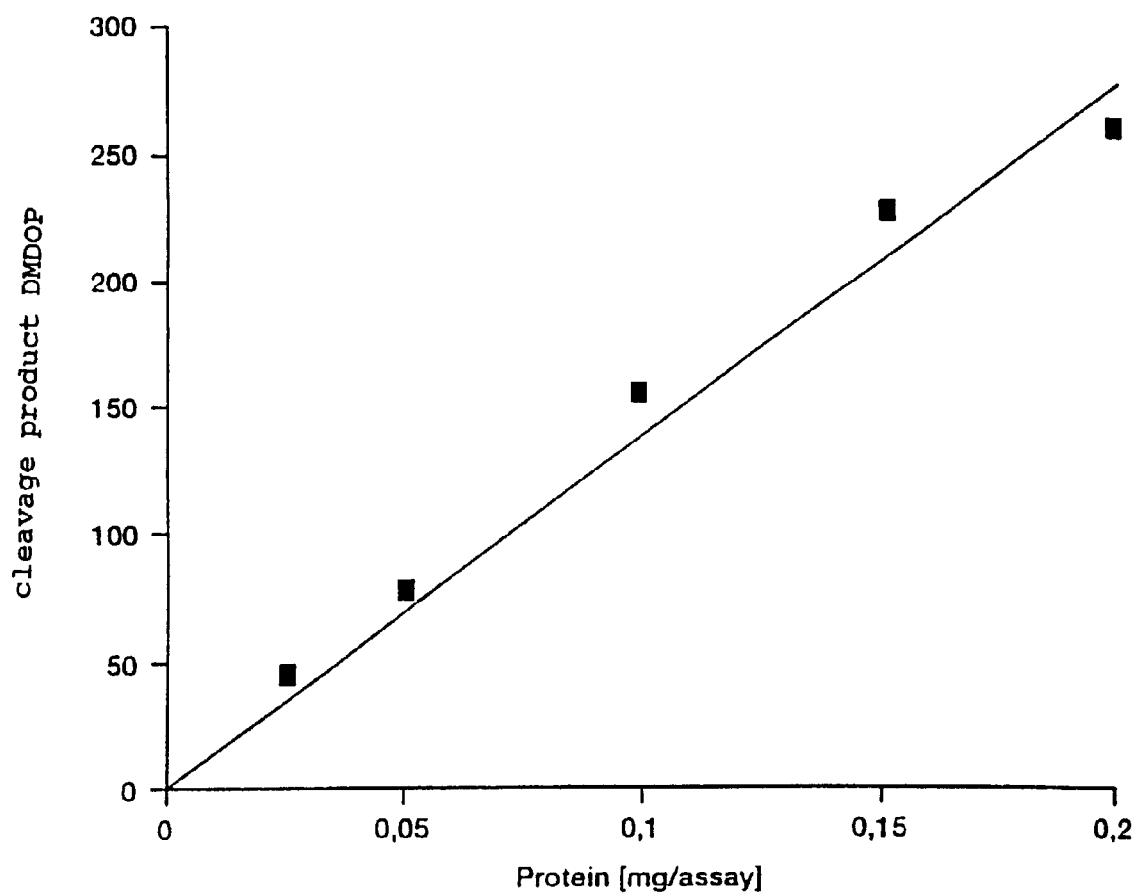

This is a Continuation of application Ser. No. 09/472,184 filed Dec. 27, 1999 now abandoned, (which in turn is a Continuation Application of Parent application Ser. No. 09/232,732 flied Jan. 19, 1999, now abandoned; which is a Continuation application Ser. No. of 08/836,046 filed Jul. 8, 1997, now abandoned from PCT/EP95/04414 filed Nov. 9, 1995. The disclosure of the prior application(s) is hereby incorporated by reference herein in its entirety.

The lipid cleavage enzyme complex (lipid cleavage enzyme; LCE) and its analogues, the subject matter of the present invention, are membranous enzymes that have previously not been described which can for example be isolated from the cell membrane fractions of human peripheral blood leucocytes or human macrophages and which cleave conjugates of pharmacologically active substances that are bound to a lipid-like carrier molecule to release the pharmacologically active substance or a monophosphate thereof. The invention also concerns the use of these conjugates which serve as substrates of this enzyme complex for the production of pharmaceutical agents that contain these conjugates as a pharmaceutically active substance. The pharmaceutical agents are suitable for the specific release and accumulation of pharmacologically active substances in appropriate target cells. In addition the invention concerns in vitro test systems which contain this enzyme complex to screen for further substrates of this enzyme complex as well as test systems for finding LCE analogues. LCE is understood as the enzyme complex, isolated enzyme as well as possible isoenzymes.

Apart from the inadequate efficacy of the therapeutically active substances used, the therapy of malignant neoplasias (carcinomas, sarcomas, haemoblastoses, haematological neoplasias), inflammatory diseases or autoimmune diseases as well as diseases caused by viruses or retroviruses such as for example AIDS, ARC (AIDS related complex), cytomegaly, herpes or hepatitis, is often accompanied by their extreme side effects. This effect is due to inadequate in vivo selectivity or the limited therapeutic range of the pharmacologically active substances used. The advantageous pharmacological in vitro properties of the pharmacologically active substances can often not be transferred to the in vivo conditions.

Therefore for years attempts have been made to modify the chemical structure of pharmacologically active substances to provide new substances which have improved properties with regard to therapeutic range. Moreover new pharmaceutical forms of administration are often developed with the aim of transporting the active substance specifically to its site of action where it is intended to display its therapeutic action. It is intended in particular to avoid undesired interactions with healthy cells. In the case of tumour cells which have corresponding surface antigens, antibodies have for example been produced that recognize these special surface antigens and thus selectively bind to the cancer cell. The antibodies are modified with suitable toxins in such a way that the toxin is released after binding to the cancer cell and the cancer cell is killed. Another alternative for improving the therapeutic range is to change the physical properties of the underlying active substance by slight modification of the pharmacologically active substance for example by producing acid or base addition salts or by preparing simple esters [for example fatty acid esters; J. Pharm. Sci. 79, 531 (1990)] in such a way that the solubility or compatibility of the active substance is improved. These slightly chemically modified compounds are often referred to as so-salled "prodrugs" since on contact with body fluids or in the liver (first pass metabolism) they are almost immediately converted into the actual therapeutically active agent.

The technical problem that forms the basis of the present invention was to find a new target which occurs as specifically as possible on or in cells that are a target for the administration of pharmacologically active substances. The target should interact with appropriate pharmaceutically active substances so that the active substances are transported as specifically as possible to these target cells, and can be recognized, bound and taken up by these. In this case the pharmaceutically active substance should be essentially composed of two components the first component being responsible for the recognition and interaction with the target (ligand-specific part) and the second component being the actual active substance (active substance-specific part) which only develops its activity after specific binding to the target molecule and the actual active agent or its monophosphate has been cleaved off intracellularly. This should avoid the undesired release of the pharmacologically active substance in the body fluids so that healthy cells are not adversely effected by the pharmacologically active agent and undesired side-effects are substantially avoided. In this connection the pharmaceutically active substance used for this purpose for the production of the pharmaceutical form should on the one hand serve as a ligand for the target and on the other hand contain the actual active pharmacological agent whereby this can also in particular be based on already known pharmaceutically active structures for which it is intended to significantly improve the therapeutic range in this manner.

It was now surprisingly found that LCE is suitable as a target, LCE being mainly located on or in malignant, activated or virus-infected cells in particular on human peripheral blood leucocytes, macrophages, kidney, adrenal or ovarian cells, cells of the lymphatic system or the lymphoid organs or cells of the brain. In the following this enzyme complex and its analogues are also abbreviated as LCE. Surprisingly LCE does not exhibit a uniform statistical distribution over all organs but is observed primarily in the membranes of certain cells which come into consideration as the target for the administration of pharmacologically active substances. A relatively very low enzyme activity was found in cardiac, bone marrow and liver cells. The homogenate and membrane fractions of cells, organs or tissues used to isolate the LCE have different specific activities or affinities of the LCE, the specific activity or affinity being strongly increased in activated cells compared to non-activated cells. This can be demonstrated for human peripheral blood leucocytes, lymphocytes and granulocytes as well as for human and non-human and murine mononuclear cells such as e.g. monocytes/macrophages.

Surprisingly a characterisitic of LCE is that it cleaves lipid-like compounds as the substrate between the lipid backbone and the linker structure of a physiologically active substance covalently bound to this bridge. Such substrates can be described by the general formula I

L-B-D  (I)

in which L represents a lipid residue, B a bridge and D represents a pharmacologically active substance or B-D represents an active substance phosphonate. Surprisingly the pharmaceutically active substances of formula I have a larger therapeutic range compared to the pharmacologically active free or unmodified substances D or —B-D. Moreover they often improve their retention time in the body, the bioavailability or the membrane permeability which is often known to be a critical factor (e.g. blood-brain barrier, cell membranes etc.) of the pharmacologically active substances. Substrates of formula I therefore serve as a carrier system (carrier) for the pharmacologically active substance. The conjugates of formula I can be referred to as intracellular drug storage, drug targeting and drug delivery systems with regard to their function. Their effect is that the pharmacologically active substance or its prodrug form is released intracellularly after oral administration, this release taking place advantageously not unspecifically in all cells, organs or tissues of the body but rather specifically in those cells that contain the LCE in the cell membrane or also partially intracellularly. However, it is particularly surprising that cleavage does not already take place during the transport of the substrate through the body fluids such as blood, serum or lymph fluid or through the liver but only on or in the respective target cells. In this manner the undesired excretion of the cleavage product by the kidney or cleavage of the substrate in the liver is avoided so that the major proportion of the active substance is transported to the respective target cells. As already stated above, such cells are in particular pathophysiologically or physiologically activated cells which come into consideration as a target for the administration of pharmacologically active substances such as for example blood leucocytes, lymphocytes, macrophages and other cell populations of the immunological lymphatic system. These are in particular activated cells (e.g. macrophages, granulocytes, lymphocytes, leucocytes, thrombocytes, monocytes etc.) which play a pathological, physiological, pathophysiological or symptomatic role in the respective disease process.

LCE is an enzyme complex which has previously not been described. It is characterized in particular in that it cleaves the compound (3'-deoxy-3'-azidothymidine)-5'-phosphoric acid-(3-dodecyl-mercapto-2-decyloxy)-propyl ester (abbreviated as AZT-DMDOPE in the following) as a substrate to form 3'-deoxy-3'-azidothymidine-monophosphate and (3-dodecylmercapto-2-decyloxy)-propanol (DM-DOP). A further preferred substrate of LCE is the compound (3'-deoxy-3'-fluorothymidine)-5'-phosphoric acid-(3-dodecyl-mercapto-2-decyloxy)-propyl ester (FLT-DMDOPE) which is cleaved into 3'-deoxy-3'-fluorothymidine-5'-monophosphate and DMDOP. Alternatively (5-fluorouridine)-5'-phosphoric acid-(3-dodecylmercapto-2-decyloxy)-propylester (5-FU-DMDOPE) is also cleaved into (5-fluorouridine)-5'-monophosphate (5-FU-MP) and DMDOP.

The preparations containing LCE that have been produced are free of phospholipase C. This has been demonstrated by the different cation dependency of the LCE activity as well as by phospholipase C-specific inhibitors which do not inhibit LCE.

An enzyme assay was established (example 6) to determine the turnover rate of AZT-DMDOPE by cell homogenates, membrane and cytosol fractions, preferably of various human cell types.

The test principle is based on a cleavage of the parent substance by the LCE into AZT-MP and the corresponding thioether lipid part. [$^{14}$C]-AZT-DMDOPE and non-radioactively labelled AZT-DMDOPE were used for this. The thioether lipid metabolite DMDOP was extracted from the mixtures (example 7) and the amount of radioactively labelled substance was measured in a liquid scintillation analyzer. Since a defined amount of [$^{14}$C]-AZT-DMDOPE was used in the enzyme assay it was possible to determine the turnover rate of the enzymatic cleavage.

The enzyme is preferably isolated from human peripheral blood leucocytes which have previously been activated by PHA or other stimulants (e.g. cytokines etc.) or from murine kidney cells. Preliminary investigations have yielded a molecular weight of about 120,000–160,000 determined by the SDS-PAGE method. Cells which contain this enzyme can be identified in a simple manner by admixing them under suitable test conditions with a solution of AZT-DMDOPE or FLT-DMDOPE and detecting the cleavage products AZT-monophosphate or FLT-monophosphate or DMDOP for example by thin layer chromatographic methods or, in the case of radioactively labelled samples by scintillatographic methods (see examples 4–7). In contrast to the biochemically related phospholipases C or D, the LCE is not inhibited by known inhibitors of phospholipase C or D nor is it activated by activators of phospholipase C or D. In contrast to phospholipase C the enzyme is activated by the substance D 609 (tricyclodecane-9-yl-xanthogenate; $C_{11}H_{15}OS_2K$) whereas D 609 inhibits phospholipase C.

In its non-phosphorylated form intracellular AZT does not have an inhibitory effect on viral reverse transcriptase (RT) (Nakashima et al., 1986, Antimicrob. Agents Chemother. 30, 933–937; Mitsuya et al., 1985 Proc. Natl. Acad. Sci. USA 82, 7096–7100). The structural analoque of thymidine is converted by successive phosphorylation by the intracellular enzymes thymidine kinase, thymidilate kinase and pyrimidine nucleoside diphosphate kinase (Yarchoan et al., 1989, N. Engl. J. Med. 321, 726–738; Toyoshima et al., 1991, Anal. Biochem. 196, 302–307) via AZT-MP and AZT-DP into the therapeutically active RT-inhibiting ATZ-TP. AZT-DMDOPE as a thioether lipid AZT conjugate was converted by intracellular enzymatic cleavage into AZT or directly into the already phosphorylated form AZT-MP. In example 8 the intracellular concentrations of phosphorylated and non-phosphorylated AZT are determined after incubation with equipotent concentrations of AZT-DMDOPE and AZT.

In addition the enzyme complex and its analogues do not exhibit a uniform statistical organ distribution in various species (e.g. human, mouse, rat, dog, ape) but are only found in membranes of certain cells, organs and tissues which serve as target cells for cleavable conjugates of formula I. The natural substrates of these enzymes are still unknown. In cytosolic fractions the LCE activity is always below or just at the limit of detection. A very low activity is for example also found in bone marrow cells which indicates a very low or even a complete absence of bone marrow toxicity of the pharmaceutically active substances of formula I used as substrates of the LCEs.

The LCE activity exhibits a linear protein and time dependency, a specific dependency on metal cations (inhibition by $Ca^{2+}$, $Zn^{2+}$ and $Mn^{2+}$) and a classical Michaelis-Menten kinetics (substrate dependency) (example 9). In addition to the higher activity of the enzyme complex in activated cells there is also a higher affinity of the LCE to its substrate under these conditions.

The isolated LCE or LCE strongly enriched from membrane fractions can also be used to screen for new potentially cleavable substrates or for substrates which occur naturally. The substrates found in this manner can then be investigated more extensively with regard to their essential structural features which are necessary for the recognition of the substrate and binding to LCE. Such identified structural properties can then be used to produce chemically modified substrates which contain these essential features as well as in addition suitable functional groups that are suitable for coupling to pharmacologically active substances.

This also enables a screening for inhibitors or activators of the lipid cleavage enzyme.

The isolated or strongly enriched enzyme can be used diagnostically when for example increased or reduced lipid cleavage enzyme activities lead in vitro or in vivo to pathological changes or when corresponding diseases or disease symptoms are associated with these pathological changes.

The LCE can also be used to produce diagnostic agents which are used to check the cleavage of these substrates when the pharmaceutically active substances are administered to patients which results in a specific and individual adaptation of the therapy modalities in these patients (drug monitoring).

Recombinant LCE can be produced by well-established methods by determining the amino acid sequence of LCE or LCE fragments and screening a human or other mammalian gene library with oligonucleotide probes that have been constructed appropriately. The found gene is then expressed by an appropriate vector in a prokaryotic or eukaryotic cell system. The recombinant LCE can then be purified by methods known in protein chemistry (see e.g. Maniatis, Molecular Cloning).

A particular characteristic of the LCE is that it can cleave compounds of the general type I:

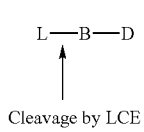

(I)

Cleavage by LCE in which L represents a lipid moiety, B represents a bridge and D represents a pharmacologically active substance or B-D denotes an active substance phosphonate. The very specific cleavage takes place between the lipid moiety and phosphate residue. An unspecific cleavage of compounds of formula I at other functional groups in the molecule is not observed.

In this connection the lipid moiety L of the conjugate of formula I represents the following residue of formula II

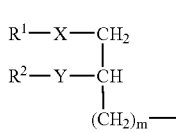

(II)

in which
- $R^1$ is a straight-chain or branched, saturated or unsaturated alkyl chain with 1–30 carbon atoms which cab be optionally substituted once or several times by halogen, $C_5$–$C_7$ cycloalkyl, phenyl, $C_1$–$C_6$ alkoxy, $C_1$–$C_6$ alkylmercapto, $C_1$–$C_6$ alkoxycarbonyl, $C_1$–$C_6$ alkylsulfinyl or $C_1$–$C_6$ alkylsulfonyl groups
- $R^2$ is hydrogen, a straight-chain or branched, saturated or unsaturated alkyl chain with 1–20 carbon atoms which can be optionally substituted once or several times by halogen, $C_5$–$C_7$ cycloalkyl, phenyl, $C_1$–$C_6$ alkoxy, $C_1$–$C_6$ alkylmercapto, $C_1$–$C_6$ alkoxycarbonyl or $C_1$–$C_6$ alkylsulfonyl groups
- X represents a valency dash, oxygen, sulphur, aminocarbonyl, oxycarbonyl, carboxyamino, carbonyloxy, carbonylamido, amidocarbonyl, a sulfinyl or sulfonyl group
- Y is a valency dash, aminocarbonyl, oxycarbonyl, carboxyamino, carbonyloxy, carbonylamido, amidocarbonyl, an oxygen or sulphur atom and
- m represents an integer between 1 and 5.

$R^1$ in the general formula II preferably denotes a straight-chain or branched $C_8$–$C_{15}$ alkyl group which can additionally be substituted by a $C_1$–$C_6$ alkoxy or a $C_1$–$C_6$ alkylmercapto group. $R^1$ in particular represents a nonyl, decyl, undecyl, dodecyl, tridecyl or tetradecyl group. Methoxy, ethoxy, butoxy and hexyloxy groups come preferably into consideration as $C_1$–$C_6$ alkoxy substituents of $R^1$. If $R^1$ is substituted by a $C_1$–$C_6$ alkylmercapto residue, then this is in particular understood as a methylmercapto, ethylmercapto, propylmercapto, butylmercapto and hexylmercapto residue.

$R^2$ preferably denotes a straight-chain or branched $C_8$–$C_{15}$ alkyl group which can additionally be substituted by a $C_1$–$C_6$ alkoxy group or a $C_1$–$C_6$ alkylmercapto group. $R^2$ in particular represents an octyl, nonyl, decyl, undecyl, dodecyl, tridecyl or tetradecyl group. A methoxy, ethoxy, propoxy, butoxy and hexyloxy group preferably come into consideration as $C_1$–$C_6$ alkoxy substituents of $R^2$. If $R^2$ is substituted by a $C_1$–$C_6$ alkylmercapto residue then this is in particular understood as a methylmercapto, ethylmercapto, butylmercapto and hexylmercapto residue.

X is preferably sulphur, sulfinyl or sulfonyl and Y is oxygen. The heteroatoms X and Y in the lipid moiety L can only be replaced in special cases by the carboxylic acid ester known from lecithin since otherwise a hydrolytic cleavage to form the corresponding lysolecithin derivatives or glycerol esters with a corresponding more rapid elimination of the pharmacologically active substance would already occur in the serum or in the liver (first pass effect). The thioether lipids and ether lipids (X, Y=O, S) of this application do not exhibit this cleavage in the serum of various species including humans.

Compounds are also preferred in which X and Y represent a valency dash, $R^2$ is hydrogen and $R^1$ represents a $C_1$–$C_{30}$ alkyl chain which can optionally be substituted by $C_1$–$C_6$ alkoxy or $C_1$–$C_6$ alkylmercapto.

m is referably 1 or 2 and particularly preferably 1.

The bridge B represents a valency dash or is expressed by the formula III

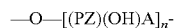 —O—[(PZ)(OH)A]$_n$- (III)

in which n can be 1, 2 or 3 but is preferably 1 or 2 and especially 1, Z is either O or S, and A is either O, S or a valency dash and preferably O.

The lipid moiety L and the phosphate bridge B have the above-mentioned meaning in which L preferably represents a residue of formula II and B is preferably a phosphate bridge of formula III. A phosphate bridge of formula III is particularly preferred in which n=1 and a lipid moiety of formula II is particularly preferred in which $R^1$ and $R^2$ represent an alkyl residue with 8–15 C atoms, X equals sulphur and Y is oxygen. Furthermore compounds are preferred in which B as a phosphonate is a constituent of the structure of the active substance in which case n=1 and A is a valency dash.

The term "pharmacologically active substance" (named D or B-D in the case of phosphonates in formula I) in this application represents an active substance within the legal pharmaceutical sense. This active substance can be an active substance of a pharmaceutical agent that has already been introduced and licenced by the pharmaceutical authorities or an active substance which is currently being registered as a pharmaceutical agent. The definition "pharmacologically active substance" also encompasses such derivatives of active substances that can be chemically modified by introducing one or several functional groups (for example such groups which enable D to be coupled to the lipid carrier moiety L such as e.g. hydroxy or amino groups). The definition also encompasses prodrug forms that are formed from the active substance D which are also physiologically active. In particular pharmacologically active substances D come into consideration whose clinical development has been discontinued or not been started due to undesired side effects or which only have a very narrow dose-effect spectrum so that the administration of the therapeutically required amount would be associated with high risks or virtually impossible to get under control.

Surprisingly it was found that the therapeutic range of a pharmacologically active substance D or B-D in the case of phosphonates of the active substance is significantly improved when the substance is coupled to a lipid-like carrier molecule. The conjugate prepared in this manner serves as a new active substance for the production of pharmaceutical forms of administration. Overall the coupling results in an increased activity of the pharmaceutically active substance D or B-D in vivo since, due to the drug-delivery transport system that is formed, the pharmacologically active substance is localized in target cells and thus the efficiency of the pharmacologically active substance is increased. This means that on the one hand the amount of pharmacologically active substance that has to be administered can be reduced or on the other hand that an increased pharmacological effect is achieved while retaining the same effective amount.

The chemical structure of the pharmacologically active substances D or B-D can in addition be modified in such a way that the substances are changed with regard to their physical or chemical properties and for example have a higher or lower lipophilicity but have essentially the same properties as the unmodified substance D or B-D with regard to their therapeutic effect. In particular it is advantageous when the substance D is chemically modified by the introduction of functional groups in such a way that it can be coupled via a suitable bridge to the lipid moiety L. This is for example achieved by the introduction of hydroxy groups which are coupled via the phosphate group B to the lipid.

The pharmacologically active substance D or B-D is a chemically or biologically based substance (antibody, peptide, protein, hormone, toxin etc.; INDEX NOMINUM, International Drug Directory, Medpharm) with a biological effect as well as derivatives thereof chemically modified by the introduction of a functional group (e.g. a hydroxy group). A prerequisite is that the pharmacologically active substance or its prodrug form are activated by this endogeneous enzyme via the cleavage of the liponucleotide by the lipid cleavage enzyme. In this connection pharmacologically active substances are preferred which after cleavage by the LCE act in vivo as an intermediate product as the pharmacologically active substance monophosphate and are further phosphorylated by cellular enzymes such as e.g. nucleoside monophosphate to nucleoside triphosphate, or are cleaved to form a free pharmacologically active substance (see example 8).

Within the sense of the invention all pharmacologically active substances come into consideration which are effective in vitro but are toxic in vivo in the therapeutic range i.e. all substances with a narrow therapeutic range which have a chemical functional group for a covalent linkage to phosphate. In addition those substances can also be used which, although at first containing no functional group in their pharmacologically active form, can have one introduced by chemical modification without a loss in the effect of the substance.

Those pharmacologically active substances are preferably used for conjugation with a lipid residue L which normally reach their active form after phosphorylation (such as in the case of nucleosides) or phosphonates of the active substance. The pharmacologically active substance phosphate is then released from the conjugate by enzymatic hydrolysis of the conjugate. The release of the phosphorylated substance is particularly important since this process can also take place in cells which do not normally have the necessary enzymes (kinases) to phosphorylate the pure pharmacologically active substance. The conjugated pharmacologically active substance that is released intracellularly or in the cell membrane by LCE can for example have a cytostatic, cytotoxic, antitumoral, antiviral, antiretroviral, immunosuppressive or immunostimulating effect.

Compounds that are suitable as pharmacologically active substances D which can be optionally converted into a derivative capable of coupling by introduction of a functional group which does not significantly influence its action which then for example slows tumour growth, is a substance which intercalates into DNA and/or RNA, inhibits topoisomerase I and II, is a tubulin inhibitor, is an alkylating agent, is a ribosome inactivating compound, is a tyrosine phosphokinase inhibitor, is a differentiation inducer, a hormone, hormone agonist or hormone antagonist, is a substance which changes pleiotropic resistance to cytostatic agents, is a calmodulin inhibitor, is a protein kinase C inhibitor, is a P-glycoprotein inhibitor, is a modulator of mitochondrially bound hexokinase, is an inhibitor of γ-glutamylcysteine synthetase or glutathione-S transferase, is an inhibitor of superoxide dismutase, is an inhibitor of reverse transcriptase of HIV-1 and HIV-2 or inhibitors of hepatitis viruses A–E.

The pharmacologically active substance D or B-D can have an antiinflammatory, antirheumatic, antiphlogistic, analgetic or antipyretic action. It can in addition be an antiarrhythmic agent, a calcium antagonist, antihistamine drug, an inhibitor of phosphodiesterase or a sympathomimetic or parasympathomimetic.

All substances are suitable as the pharmacologically active substances D or B-D which have a short half-life, in particular also compounds with different organ, tissue or cell half-lives, a poor bioavailability i.e. a poor resorption, high liver cleavage or rapid elimination, poor membrane penetration (e.g. cell membrane, blood-brain barrier), bone marrow toxicity or other limiting organ toxicities (e.g. cardiotoxicities, liver toxicities, nephrotoxicities, neurotoxicities etc), whose active concentration in vivo is too low. In addition those substances are suitable which interact specifically with the cell nucleus of the target cells and interfere with the molecular process at the DNA or RNA level such as e.g. antisense oligonucleotides, DNA fragments and those which can be used for gene therapy.

Pharmacologically active substances D in formula I are for example: AZT (azidothymidine), FLT (fluoro-thymidine), 5-fluorouracil, 5-fluorouridine, 6-MPR, fludarabin, cladribin, pentostatin, ara-C, ara-A, ara-G, ara-H, Acyclovir, Ganciclovir, doxorubicin, 4'-epi-doxorubicin, 4'-deoxy-doxorubicin, etoposide, daunomycin, idarubicin, epirubicin, mitoxantron, vincristine, vinblastine, Taxol, colchicine, melphalan, 3'-deoxy-2-fluoro-adenosine, FdA, 5-ethinyluracil-9-β-D-arabinofuranoside, 5-propinyluracil-9-β-D-arabinofuranoside, d4T, ddU, ddI, ddA, d2T, 2'-deoxy-2',2'-difluorocytidine, 5-trifluoromethyl-2'-deoxyuridine, 5-chloro-2',3'-dideoxy-3'-fluorouridine, 3'-deoxy-3'-fluoromyoinositol, neplanocin A, ribavirin, myoinositol, fialuridine, 3TC (Lamivudine), doxifluridine, Tegafur, hypericin, pseudohypericin, Usevir, Famciclovir, Penciclovir, Foscarnet, Carvedilol, actinomycin A, bleomycin, daunorubicin, floxuridine, mithramycin, mitomycin C, mitoxanthrone, streptozotocin, vindesin, netilmycin, amikacin, gentamycin, streptomycin, kanamycin A, tobramycin, neomycin B, plicamycin, papamycin, amphotericin B, vancomycin, idoxuridine, trifluridine, vidarabin as well as morphines, prostaglandines, leukotrienes or cyclosporins. Moreover terfenadin, dexamethasone, terbutalin, prednisolone, fenoterol, orciprenaline, salbutamol, isoprenaline, muscarine, bupranolol, oxyphenbutazone, oestrogen, salicylic acid, propranolol, ascorbic acid, spongiadiol, diclofenac, isospongiadiol, flufenamic acid, digoxin, 4-methyl-aminophenazone, allopurinol, theophylline, epoprostenol, nifedipine, quinine, reserpine, methotrexate, chloroambucil, spergualine, ibuprofen, indomethacin, sulfasalazine, penicillinamine., chloroquine, azathioprine also come into consideration.

Pharmacologically active substances B-D in formula I are. for example PMEA and other acyclic nucleoside phosphonate analogues, quinoline-phosphonic acids, MP-101, fostedil, HAB-439, 2-amino-7-phosphonoheptanoic acid, fosfosal, fosphenytoin, atrinositol, cyplatate, difficidin, fosquidone, alafosfalin, foteumstine, etoposide, encyt/E, 4-oxo-S-phosphono-D-norvalin and other NMDA-antagonist phosphonates.

Preferred pharmacologically active substances are for example also peptides, proteins and oligonucleotides such as e.g. corticotropin, calcitonin, desmopressin, gonadotropin, goserelin, insulin, zypressin, beta-melanotropin, alpha-melanotropin, muramyldipeptide, oxytocin, vasopressin, FK-506, octreotide or enalkiren.

The above-mentioned pharmacologically active substances and the conjugates to be prepared therefrom only represent examples and do not limit the inventive idea.

Compounds of formula I and the production thereof are for example described in the applications WO 92/03462, WO 93/16092, WO 93/16091, WO 94/03465, PCT/EP94/02123, DE 4402492, DE 4418690 as well as for example in WO 91/19726; EP 0 350 287; U.S. Pat. Nos. 5,223,263; 5,194,654; 4,921,951; 4,622,392; 4,291,024; 4,283,394. In the case of antivirally effective nucleosides lipid derivatives (diacylglycerol nucleosides) and their use in liposomal form are described in EP 0 350 287 and U.S. Pat. No. 5,223,263. An uptake of the substance preferably in the form of liposomes by cells of the reticulo-endothelial system (RES) e.g. macrophages and monocytes should be possible.

It was possible to show by appropriate comparative experiments that the therapeutic effects in vivo of the diacylglycerol conjugates known from EP 0 595 133 are inferior to the thioether or etherlipid conjugates from WO 92/03462. This is due to unspecific hydrolysis of the fatty acid esters which does not only take place at the site of action. In contrast the non-hydrolysable thioether and ether residues exhibit significant advantages since a substance with biological action or appropriate intermediate products are only released in the membranes of the target tissue or intracellularly by the special enzyme (LCE).

The conjugates of formula I (L-B-D) exhibit significant advantages in comparison with the unconjugated pharmacologically active substance D or B-D . The specific carrier (L-B- or L) covalently bound to the pharmacologically active substance improves the bioavailability of the poorly resorbed pharmacologically active substances, the tolerance of potentially toxic active molecules, the retention time of rapidly eliminated or metabolized pharmaceutical agents and the membrane penetration of compounds with poor membrane permeability (e.g. blood-brain, cells etc.). The enzymatic cleavage in vivo into carrier and pharmacologically active substance D (or substance derivative) or into carrier and pharmacologically active substance phosphate (D-monophosphate) or phosphonate B-D usually does not occur in the serum but only intracellularly. In addition the carrier moiety with its lecithin-like structure, which is essential for the claimed effect, improves the penetration or membrane permeability of the pharmacologically active substance and exhibits a depot effect in many cases. Moreover the gastrointestinal tolerance of the lipid conjugates L-B-D is considerably better than that of the pure pharmacologically active substances D. The lipid conjugate also exhibits a better penetration through membrane structures during resorption and thus it is more able to overcome the resorption barriers. The same also applies to penetration e.g. of the blood-brain barrier by facilitated diffusion or possibly active transport. Conjugates of formula I with a lipid moiety as limited by formula II are particularly preferred which cleave off a substance with biological activity by enzymatic hydrolysis with the lipid cleavage enzyme which leads to less side effects in vivo than after administration of the pharmacologically active substance alone.

In addition the in vivo distribution is improved by a better binding of the conjugate to plasma and tissue proteins. The conjugate is primarily oxidized by normal biotransformation from a thioether (X=S) to a sulfoxide (X=SO) which, however, due to the equipotent action of the sulfoxide in comparison to the thioether, does not represent a disadvantage. The slow release of the pharmacologically active substance from the conjugate ensures a low level of active substance that is, however, constant over a longer period of time and thus improves the efficacy or avoids toxic side-effects. The released pharmacologically active substance in the form of a monophosphate no longer penetrates out of the cell due to its high hydrophilicity.

The total body, cell and the organ half-lives of the pharmacologically active substance are considerably extended by the conjugation due to the longer retention time of the conjugate in the organism. Due to the lack of LCE activity for cleavage in serum and in some organs, almost no or only slight bone marrow and organ toxicity can be observed. It is particularly advantageous that the conjugates of formula I are specifically accumulated in various target organs, tissues or cells.

The compounds of formula I can be used as active substances for the production of pharmaceutical agents which can be used for all diseases in which a high level of pharmacologically active substance in cells, organs or tissues is required or is beneficial. An essential requirement for this transport system denoted "drug-storage-delivery-targeting" is that the cells which are to respond in accordance with the intended therapy have the lipid cleavage enzyme in the inner or outer cell membrane so that the active substance binds to the LCE in a first step and is subsequently transported through the cell membrane into the interior of the cell in the process of which the active substance is cleaved to form the physiologically active substance either essentially simultaneously with transport through the cell membrane or even later partially within the cell. Intracellular cleavage takes place especially in those cases in which the LCE is also located within the cell. Within the sense of the invention the cleavage of the active substance linked with the intracellular release of the pharmacologically active substance can also occur such that either the physiologically or pharmacologically active substance is formed directly in this process or an appropriate precursor of this substance (prodrug form). Suitable target cells are for example blood leucocytes, (PBLs), monocytes, kidney cells or macrophages and cells of the immunological lymphatic system.

The effect of compounds of formula I is in particular immunomodulating, para/sympatholytic, /sympathomimetic, centrally and/or peripherally muscle-relaxing; antihypertensive, antihypotensive, antiobstructive, analgetic, anti-phlogistic, antiemetic, anti-inflammatory, antiallergic, antiasthmatic, antipyretic, antiulcerative, antacidic, anti-anginal, antiarrhythmic, antipsychotic, antidepressive, antiepileptic, anticonvulsive, antiparkinsonoid, antihistaminergic, antimuscarineric, antiserotoninergic, antigabaergic, antiadrenergic, anticholinergic, glycosidic, chronotropic, bathmotropic, dromotropic, inotropic, diuretic, antidiuretic, uricosuric, uricostatic, antihypolipidaemic, antifibrinogenic, antidiabetic, hypoglycaemic, antioestrogenic, antiandrogenic, antigestagenic, antiosteoporetic, thyreostatic, bone-growth stimulating, narcotic, anaesthetic, antihypnotic, anti-infectious, antibiotic, antituberculostatic or haematopoetic or they represent a vitamin.

The advantageous effect of one of the compounds according to the invention can be increased by combination with suitable pharmaceutical agents or combination of two different conjugates of the present application.

The effect of a cytostatic or cytotoxic conjugate of this application can for example be increased by combination with other cytostatic or cytotoxic compounds preferably when components with different mechanisms of action are used or a combination of a cytostatic or cytotoxic conjugate with an antiviral conjugate (synergism e.g. in the case of AIDS).

The conjugate combinations are especially suitable according to the invention in which one component has cytostatic or cytotoxic potential and the other component overcomes for example multi drug resistance or a component inhibits reverse transcriptase of HIV and the other component inhibits the protease for example or both liponucleotides of the combination do not exhibit cross-resistance. Compounds of formula I and their pharmaceutical preparations can also be used for the production of pharmaceutical agents which are suitable for the treatment and prophylaxis of various diseases in combination with other pharmaceutical agents.

Alkali, alkaline-earth and ammonium salts of the phosphate group come above all into consideration as possible salts of the compounds of the general formula I. Lithium, sodium and potassium salts are preferred as the alkali salts. Magnesium and calcium salts come in particular into consideration as alkaline-earth salts. Ammonium salts are understood according to the invention as salts which contain the ammonium ion that can be substituted up to four times by alkyl residues with 1–4 carbon atoms and/or by aralkyl residues preferably by benzyl residues. In this case the substituents can be the same or different.

The compounds of the general formula I can contain basic groups in particular amino groups which can be converted using suitable inorganic or organic acids into acid addition salts. Acids which come for example into consideration are: hydrochloric acid, hydrobromic acid, sulphuric acid, phosphoric acid, fumaric acid, succinic acid, tartaric acid, citric acid, lactic acid, maleic acid or methanesulfonic acid.

In addition to the compounds of the general formula I and the specifications according to formula II and III this application also claims tautomers thereof and their physiologically tolerated salts of inorganic and organic acids or bases as well as processes for their production and pharmaceutical agents containing these compounds.

Since the compounds of the general formula I contain asymmetric carbon atoms all optically active forms and racemic mixtures of these compounds are also a subject matter of the present invention.

This application also concerns new liponucleotides. The synthesis of these conjugates is exemplified in examples 14–16. The LCE also cleaves 2-chloro-2'-deoxy-adenosine conjugates (cladribin conjugates) of formula V, 9-(β-D-arabino-furanosyl)-2-fluoroadenine conjugates (fludarabine conjugates) of formula VI, 3-(2-deoxy-β-D-erythro-pentofuranosyl)-3,6,7,8-tetrahydroimidazo [4,5-d] [1,3] diazepin-8-ol conjugates (pentostatin conjugates) of formula VII. The said compounds can be used therapeutically better than the corresponding nucleosides alone since they have a very good efficacy and a large therapeutic range and have the same advantages as the above-mentioned derivatives of formula I:

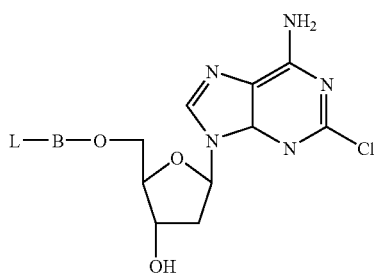

(V)

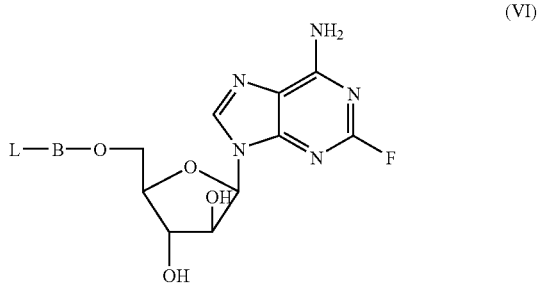

(VI)

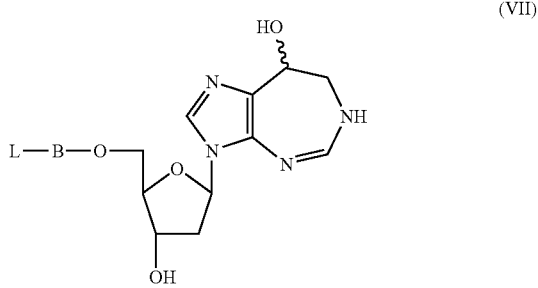

(VII)

Within the sense of the present invention the following active substances are used in particular as compounds of formula I for producing pharmaceutical agents:
1. (3'-deoxy-3'-azidothymidine)-5'-phosphoric acid-(3-dodecyl-mercapto-2-decyloxy)-propyl ester
2. (3'-deoxy-3'-azidothymidine)-5'-phosphoric acid-(3-undecyl-mercapto-2-undecyloxy)-propyl ester 3. (3'-deoxy-3'-fluorothymidine)-5'-phosphoric acid-(3-dodecyl-mercapto-2-decyloxy)-propyl ester
4. (3'-deoxy-3'-fluorothymidine)-5'-phosphoric acid-(3-undecyl-mercapto-2-undecyloxy)-propyl ester
5. (2',3'-dideoxycytidine)-5'-phosphoric acid-(3-dodecyl-mercapto-2-decyloxy)-propyl ester
6. (2',3'-dideoxyinosine)-5'-phosphoric acid-(3-dodecyl-mercapto-2-decyloxy)-propyl ester
7. (3'-deoxythymidine)-5'-phosphoric acid-(3-dodecyl-mercapto-2-decyloxy)-propyl ester
8. (5'-fluorouridine)-5'-phosphoric acid-(3-dodecyl-mercapto-2-decyloxy)-propyl ester
9. (6-mercaptopurine-9-β-D-ribofuranoside)-5'-phosphoric acid-(3-dodecylmercapto-2-decyloxy)-propyl ester
10. (5-trifluoromethyluridine)-5'-phosphoric acid-(3-dodecyl-mercapto-2-decyloxy)-propyl ester
11. (1-β-D-arabinofuranosyl-5-ethinyluracil)-5'-phosphoric acid-(3-dodecyl-mercapto-2-decyloxy)-propyl ester
12. (2'-deoxy-5-propinyluridine)-5'-phosphoric acid-(3-dodecyl-mercapto-2-decyloxy)-propyl ester
13. 2'-(9-{[(1-hydroxymethyl)ethoxy]methyl}guanine) phosphoric acid-(3-dodecyl-mercapto-2-decyloxy)-propyl ester
14. 2'-[9-(ethoxymethyl)guanine])phosphoric acid-(3-dodecyl-mercapto-2-decyloxy)propyl ester

EXAMPLE 1

Enzymatic Cleavage of AZT-DMDOPE 10 mg (3'-deoxy-3'-azidothymidine)-5'-phosphoric acid-(3-dodecyl-mercapto-2-decyloxy-propyl ester (AZT-DMDOPE) is suspended in 0.5 ml 0.1 M Tris buffer solution and incubated for 15 hours at 37° C. after addition of the enzyme (0.5 mg phosphodiesterase and 0.1 mg phospholipase/nuclease). Subsequently the solution is examined by thin layer chromatography. After addition of 5 drops of saturated NaHCO₃ solution it was incubated for a further 6 hours at 37° C. and subsequently the solution was examined by thin layer chromatography.

The solution was examined for the formation of possible cleavage products (AZT, AZT-monophosphate, DMDOP and lipid monophosphate) by thin layer chromatography using various eluting agents.

The Following Enzymes Were Used in the Above-Mentioned Test:

a) Phospholipase C from *Bacillus cereus*, 2000 U/0.5 ml, Boehringer Mannheim GmbH
b) Phospholipase D, type I, from cabbage, 150–300 U/mg, Sigma
c) Phosphodiesterase from calf spleen, 2 U/mg, Boehringer Mannheim GmbH
d) Phosphodiesterase from snake venom, Boehringer Mannheim GmbH
e) Nuclease from *Staphylococcus aureus*, 15,000 U/mg, Boehringer Mannheim GmbH
f) LCE (lipid cleavage enzyme)

Result

The following Table shows that a weak fluorescence quenching at the level of the lipid phosphate is only found in the case of phospholipase D. In none of the cases a)–e) used as reference enzymes was AZT or AZT monophosphate formation detected. Apart from the unchanged AZT-DMDOPE no additional spot was found in these experiments within the detection limit.

| Enzyme | Fluorescence quenching TLC |
| --- | --- |
| Phospholipase C | negative |
| Phospholipase D | weak |
| Phosphodiesterase from calf spleen | negative |
| Phosphodiesterase from snake venom | negative |
| Nuclease from Styphylococcus aureus | negative |
| LCE | positive |

EXAMPLE 2

FIGURE LEGENDS

FIG. 1: This figure shows the activity of the LCE which was obtained from the membrane fraction of human PHA-stimulated peripheral blood leucocytes relative to the protein concentration. There is a linear relationship between the protein concentration and the amount of the cleavage product DMDOP formed.

Figure 2:
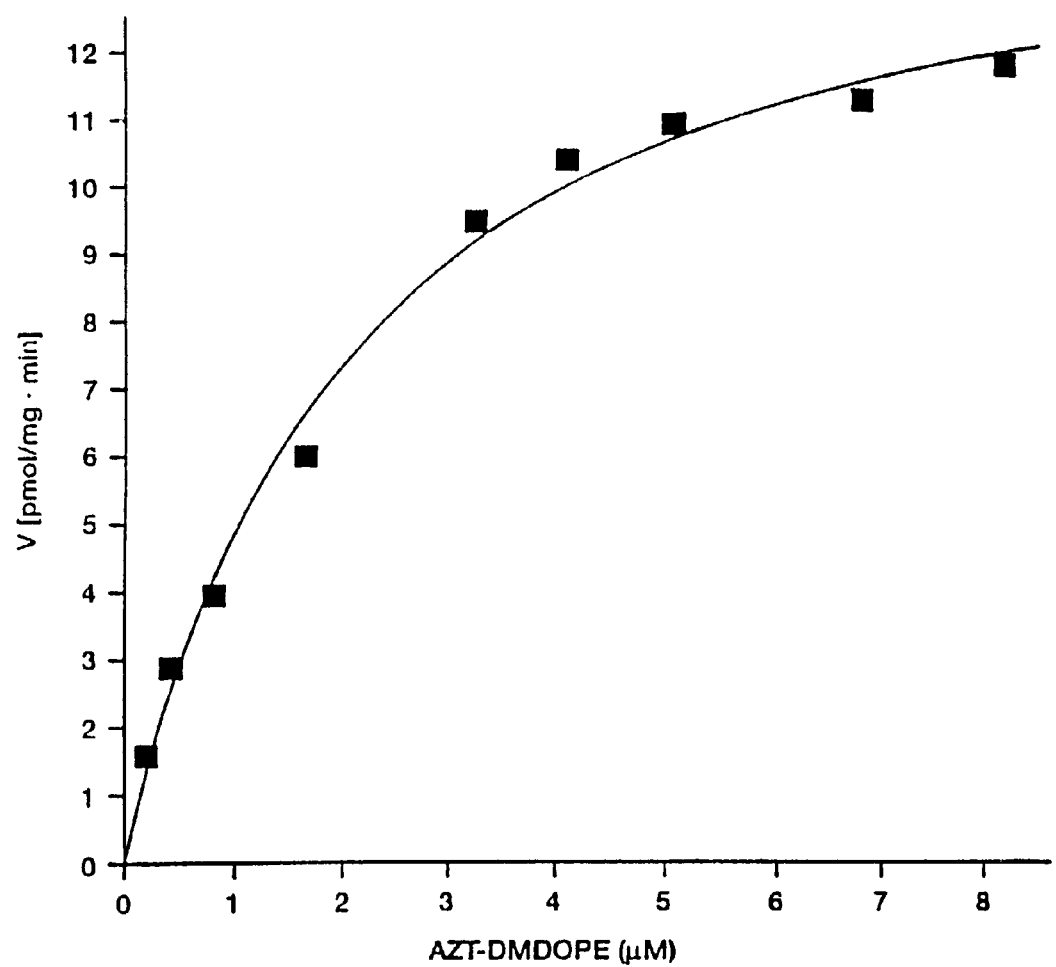

FIG. 2: This figure shows the substrate kinetics (Michaelis-Menten kinetics) of the LCE which was obtained from the membrane fraction of human, PHA-stimulated peripheral blood leucocytes.

Figure 3:
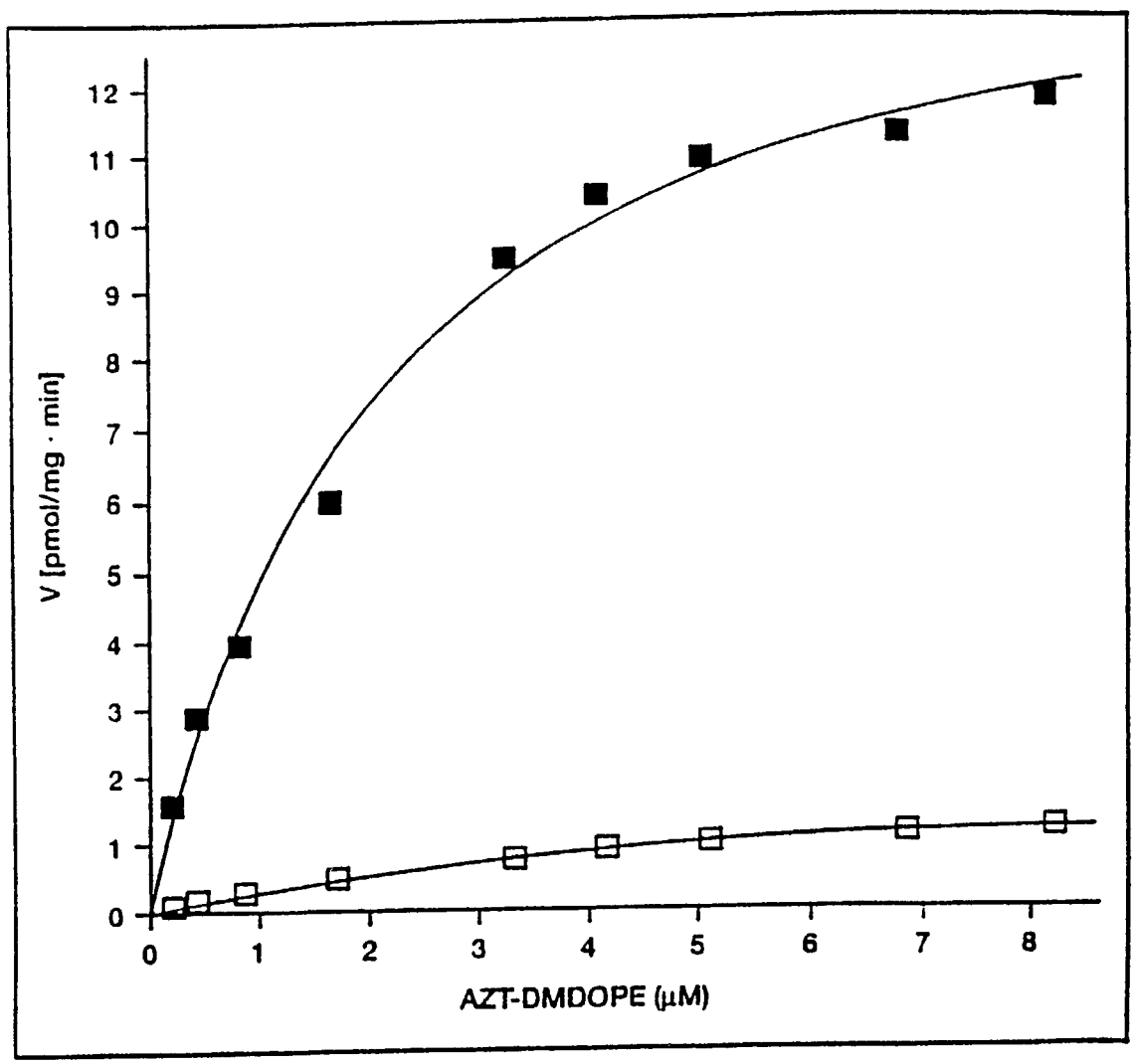

FIG. 3: This figure shows the substrate kinetics (Michaelis-Menten kinetics) of the LCE which was obtained from the membrane fraction of human, PHA-stimulated peripheral blood leucocytes [■] and from quiescent (non stimulated) peripheral blood leucocytes [□].

Figure 4:
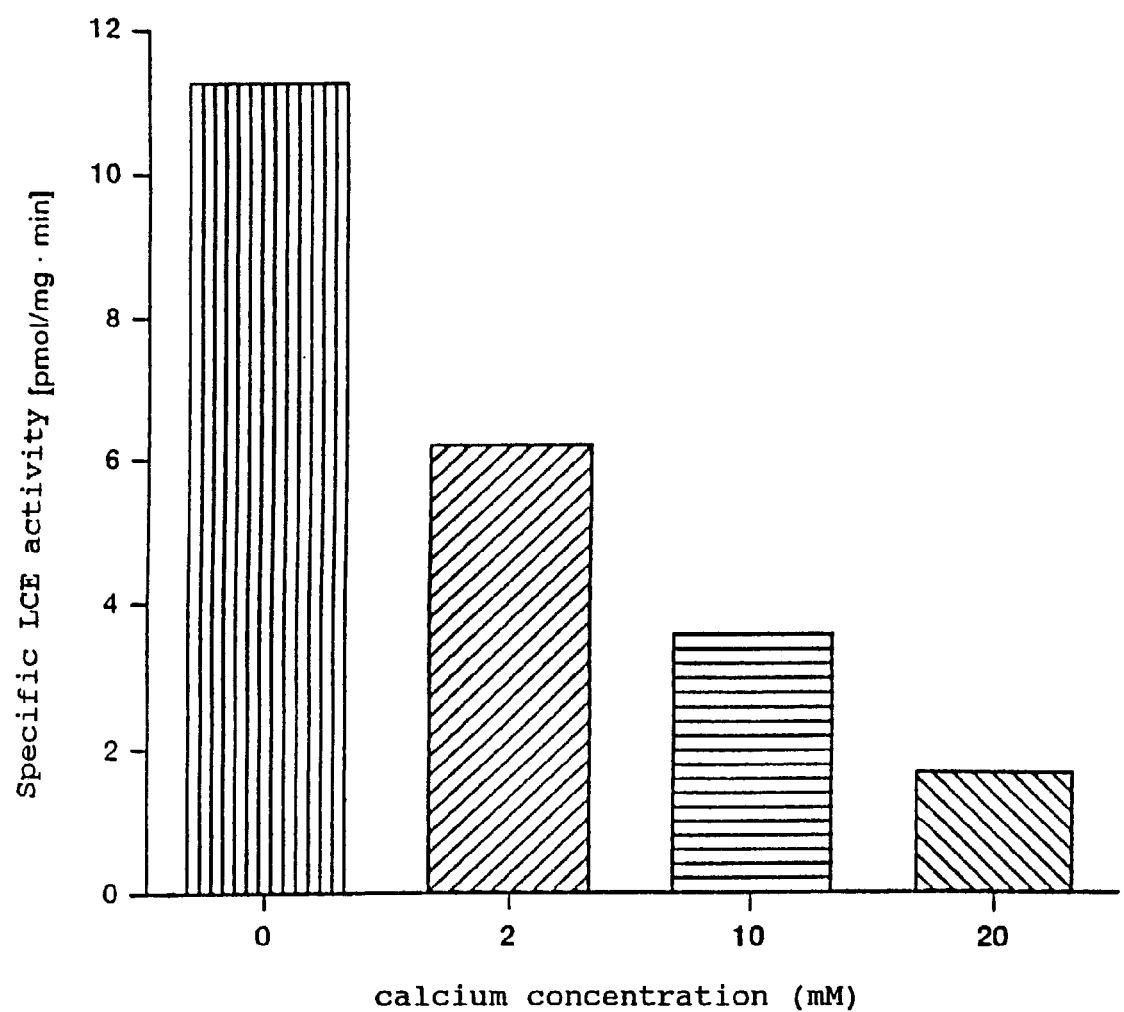

FIG. 4: This figure shows the dependence of the specific enzyme activity of the LCE which was obtained from the membrane fraction of human, PHA-stimulated peripheral blood leucocytes on the calcium ion concentration.

Figure 5:
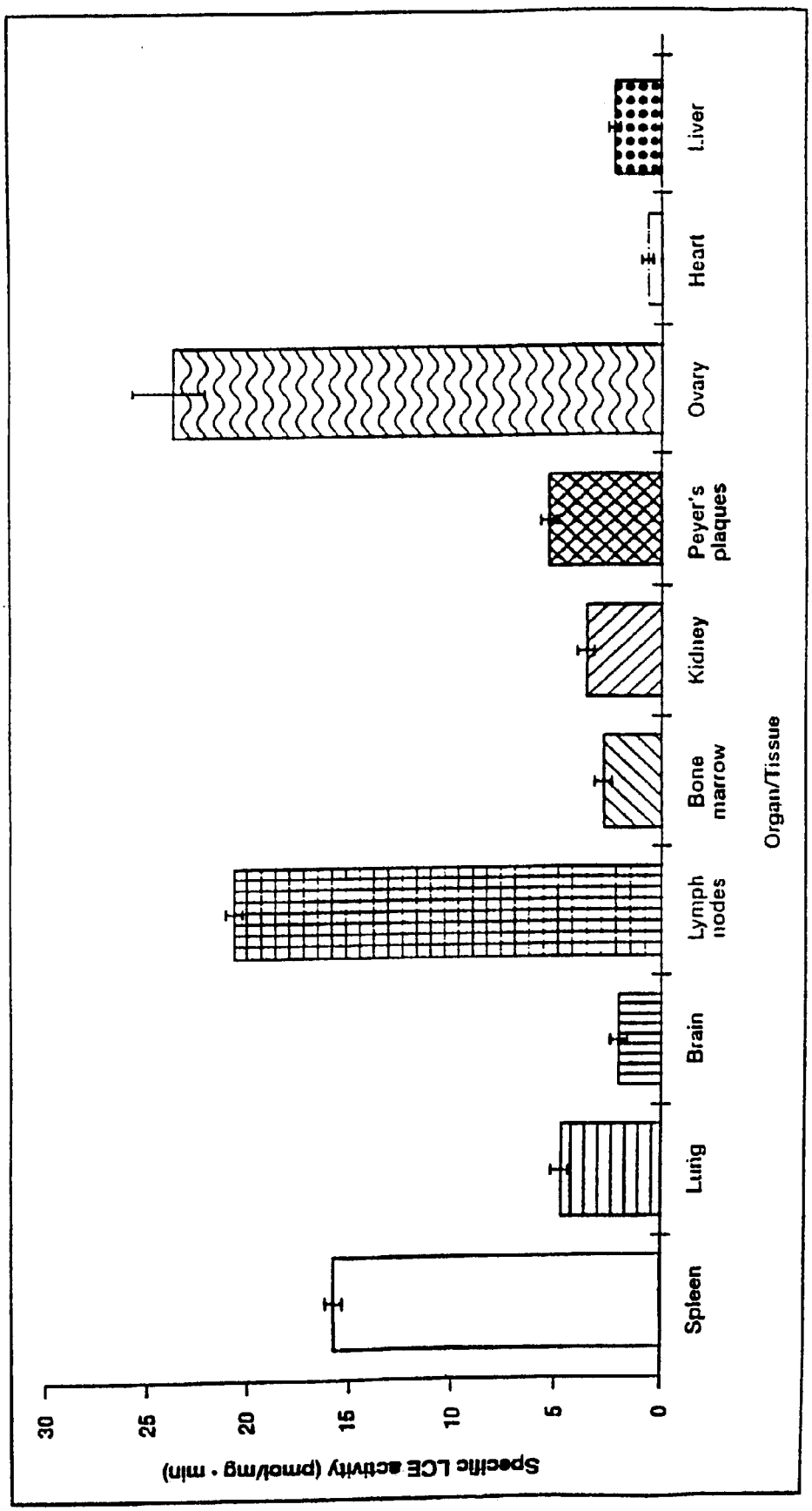

FIG. 5: This figure shows the organ-specific and tissue-specific distribution of the LCE of cell membrane preparations in the untreated dog.

Figure 6:
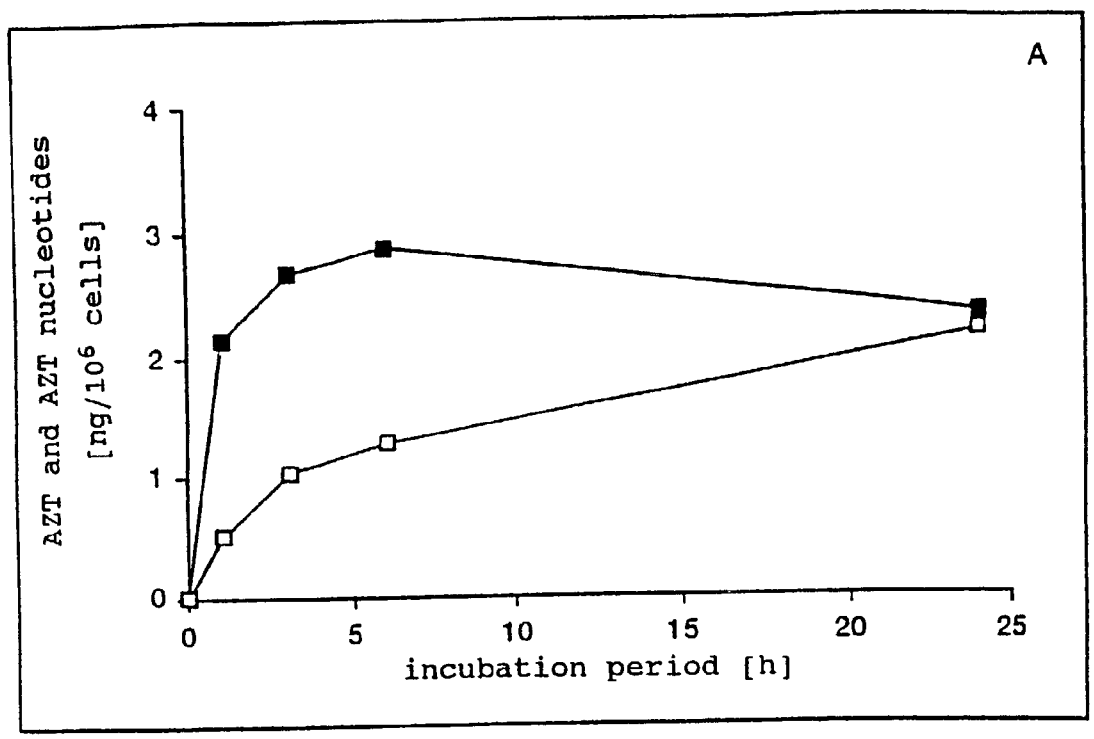
Figure 6:
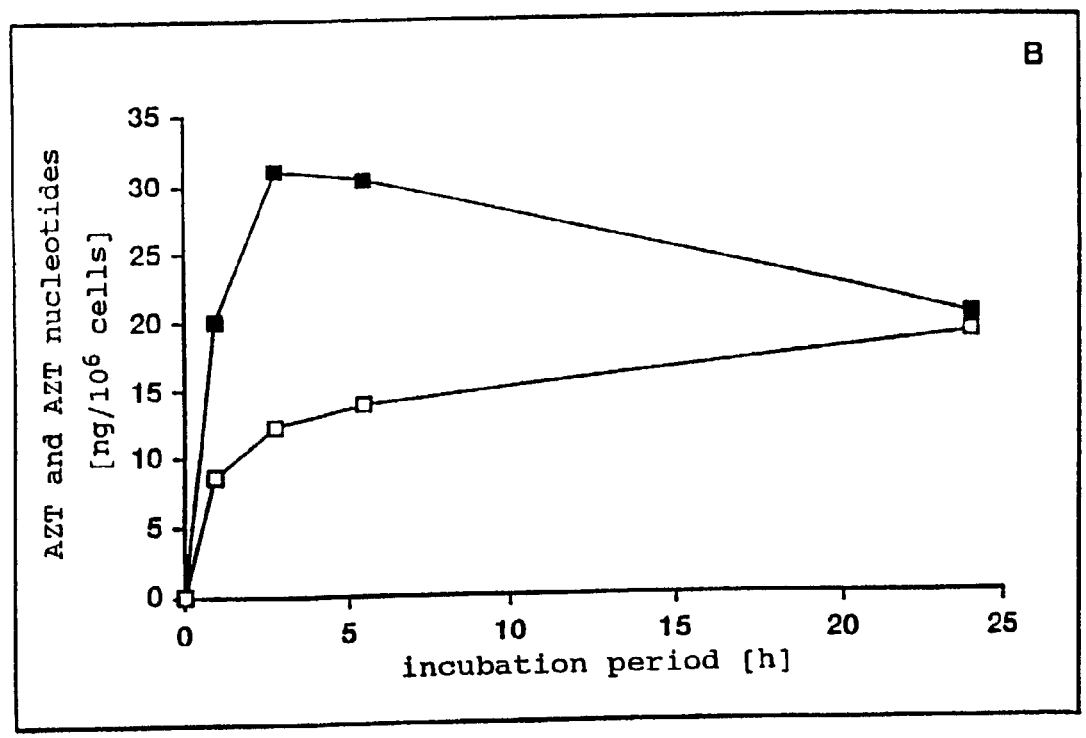

FIG. 6: Intracellular concentrations of AZT and AZT nucleotides in stimulated human PBL after 1, 3, 6 and 24 h incubation with:
(A) 0.03 μg AZT/ml (■) or 1 μg AZT-DMDOPE/ml (□)
(B) 0.3 μg AZT/ml (■) or 10 μg AZT-DMDOPE/ml (□)
(means, n=2 determinations)

Figure 7:
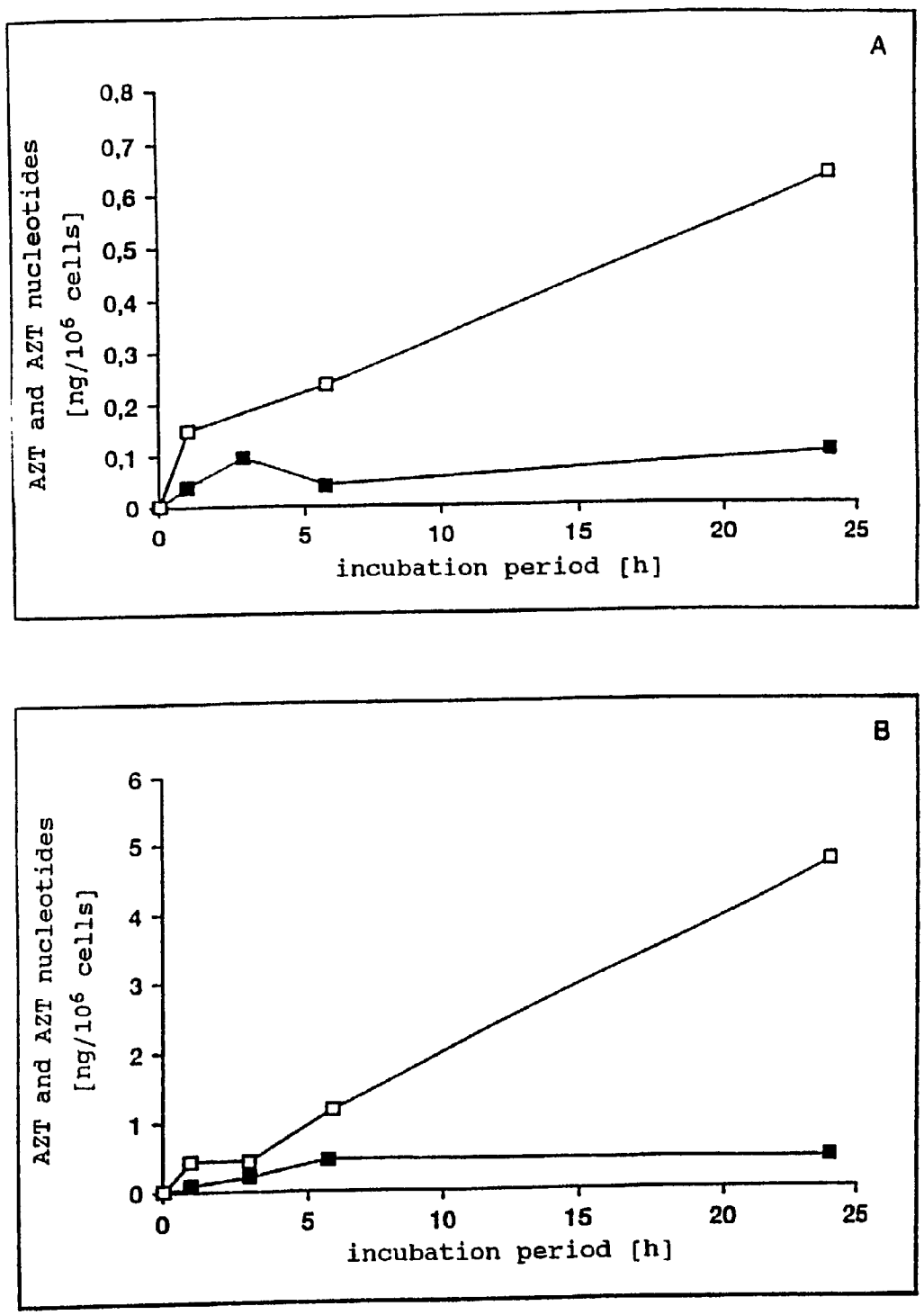

FIG. 7: Intracellular concentrations on AZT and AZT nucleotides in non-stimulated human PBL after 1, 3, 6 and 24 h incubation with:
(A) 0.03 μg AZT/ml (■) or 1 μg AZT-DMDOPE/ml (□)
(B) 0.3 μg AZT/ml (■) or 10 μg AZT-DMDOPE/ml (□)
(means, n=2 determinations)

Figure 8:
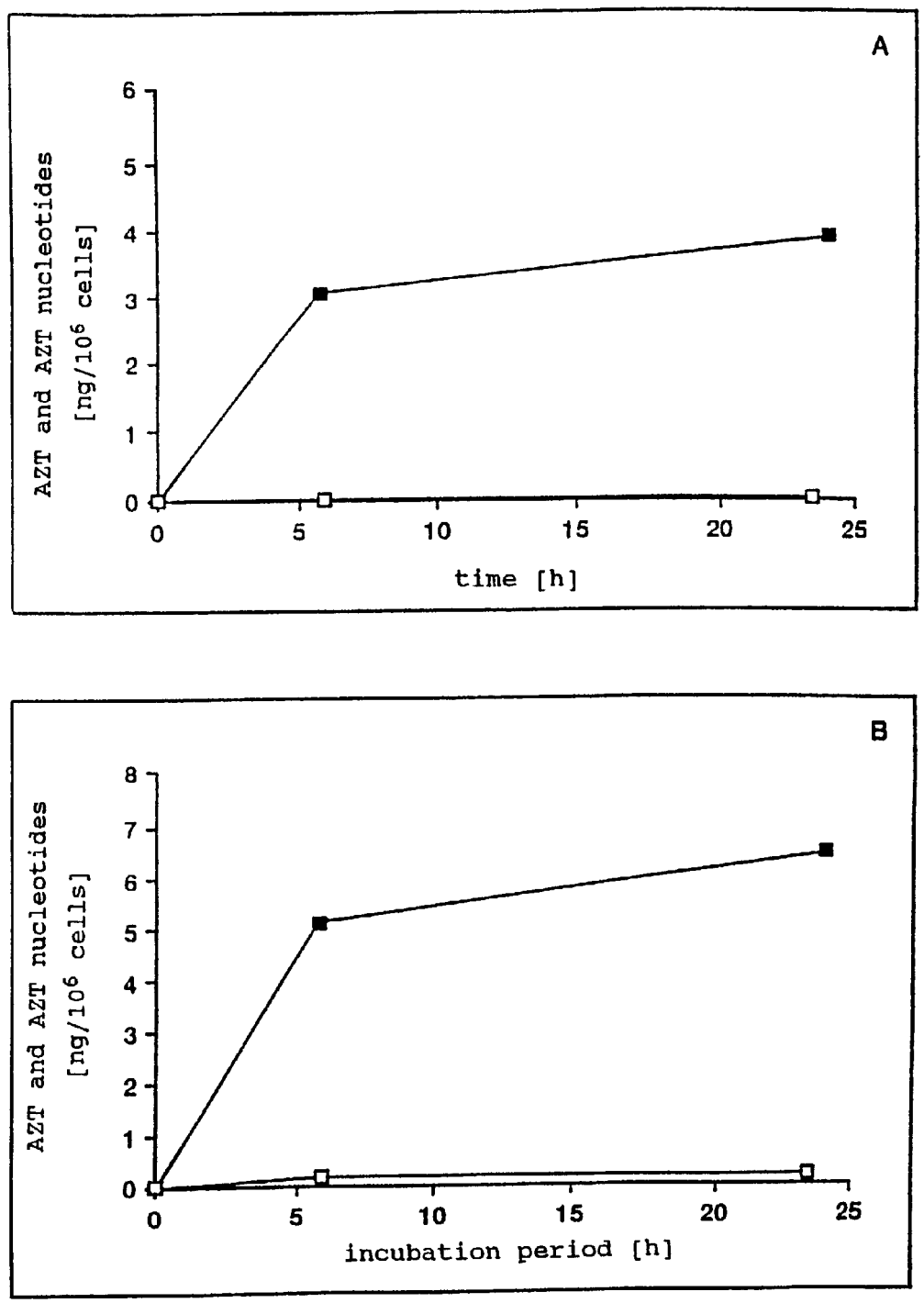

FIG. 8: Intracellular concentrations of AZT and AZT nucleotides in stimulated human PBL after 6 and 24 h incubation with 1 μg AZT-DMDOPE/ml (A) and 10 μg AZT-DMDOPE/ml (B):
■ treatment with alkaline phosphatase
□ no treatment with alkaline phosphatase (means, n=determinations)

Figure 9:
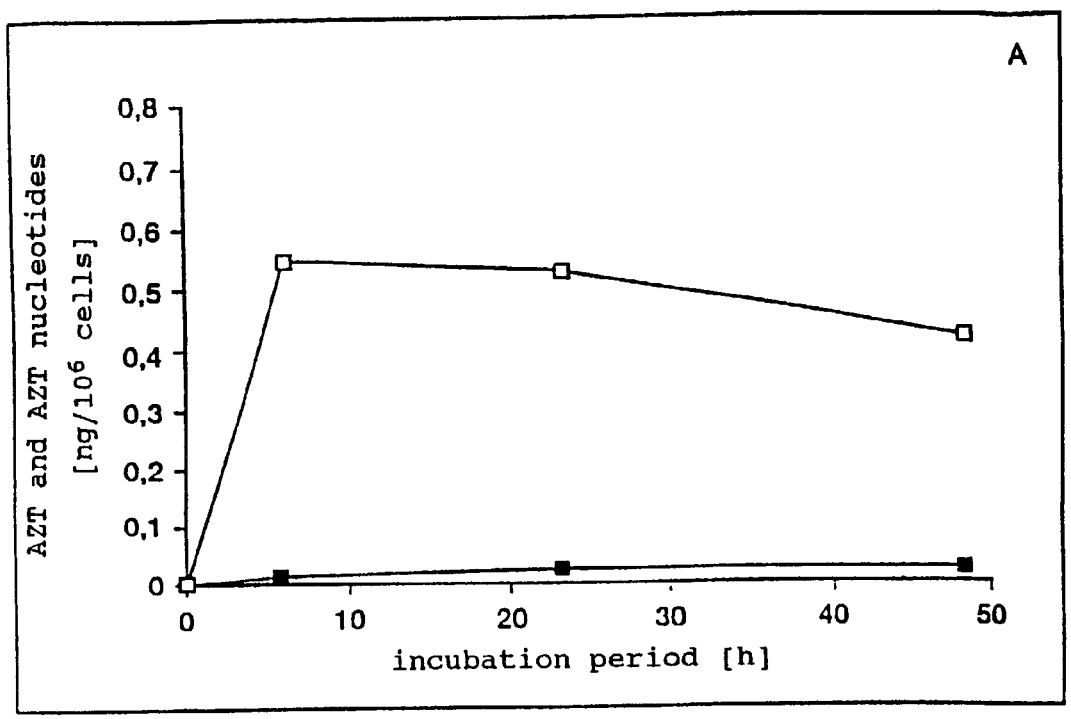
Figure 9:
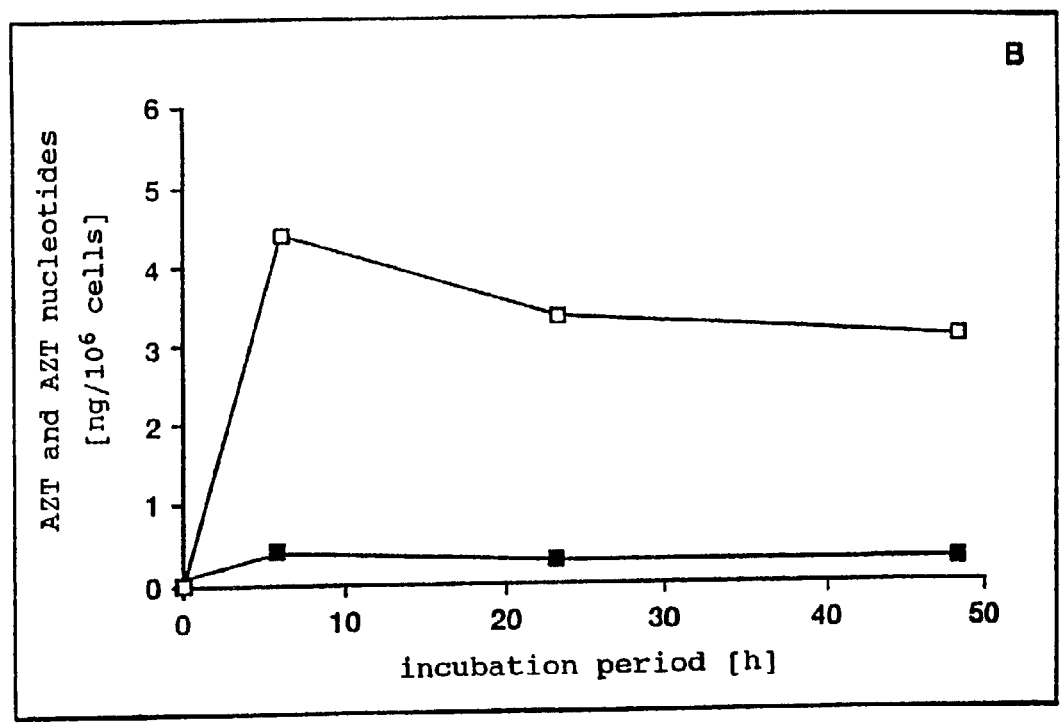

FIG. 9: Intracellular concentration of AZT and AZT nucleotides in P3X63-Ag8.653 cells after 6, 24 and 48 h incubation with:
(A) 0.03 μg AZT/ml (■) or 1 μg AZT-DMDOPE/ml (□)
(B) 0.3 μg AZT/ml (■) or 10 μg AZT-DMDOPE/ml (□)
(means, n=2 determinations)

Figure 10:
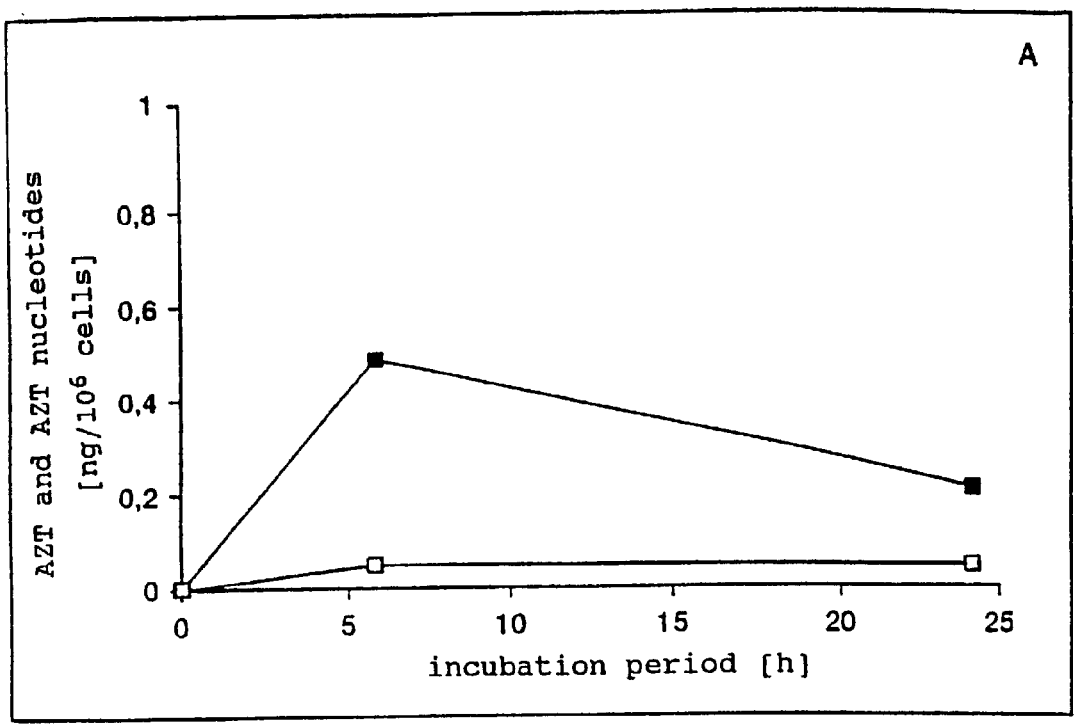
Figure 10:
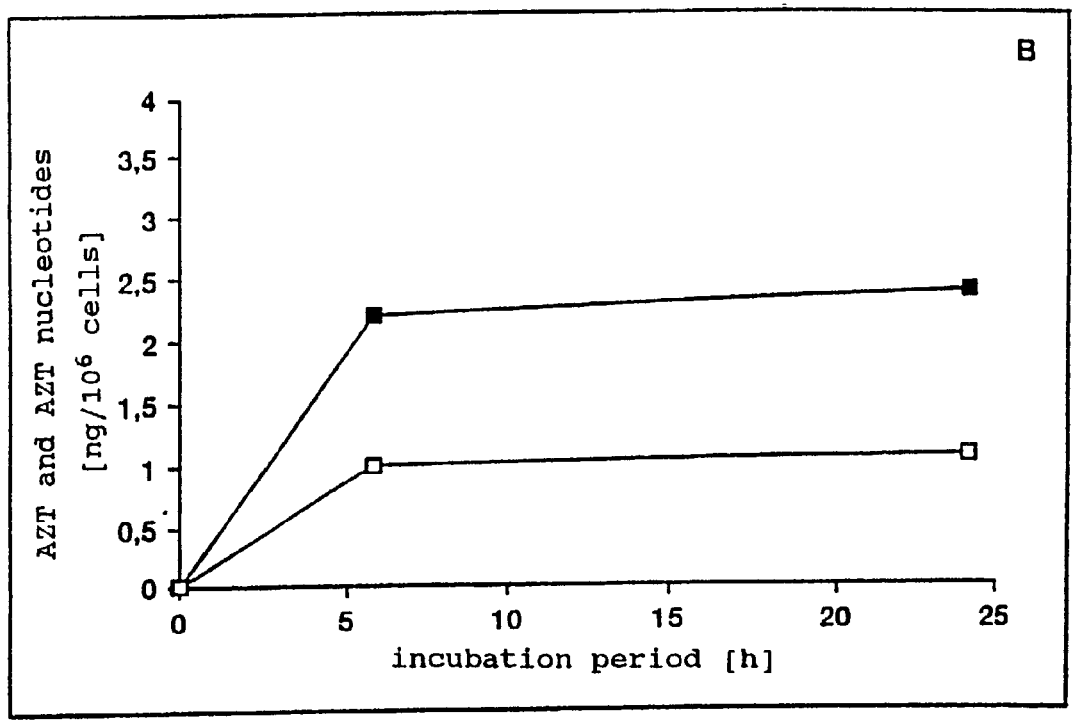

FIG. 10: Intracellular concentration of AZT and AZT nucleotides in P3X63-Ag8.653 cells after 6 and 24 h incubation with 1 μg BM 21.1290 Na/ml (A) and 10 μg AZT-DMDOPE/ml (B):
- ■ treatment with alkaline phosphatase
- □ no treatment with alkaline phosphatase (means, n=determinations)

Figure 11:
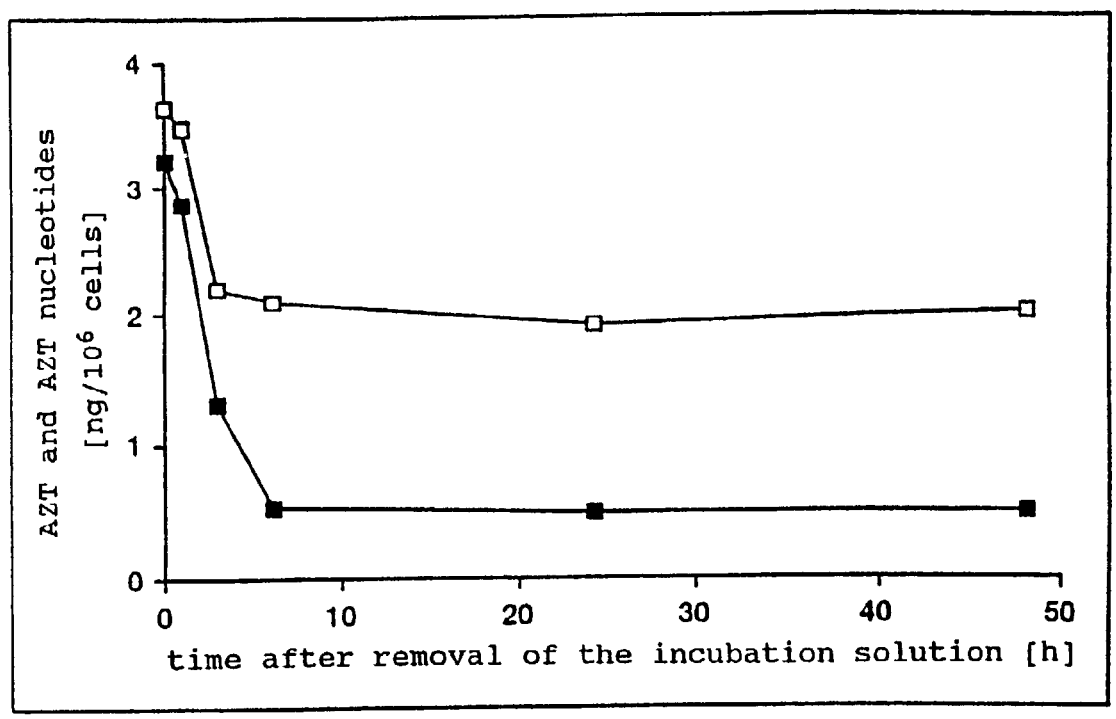

FIG. 11: Intracellular decay kinetics of AZT and AZT nucleotides in stimulated human PBL after 24 h incubation with 0.3 μg AZT/ml(A) or 10 μg AZT-DMDOPE/ml (B). Intracellular concentration of AZT and AZT nucleotides 1, 3, 6, 24 and 48 h after removing the AZT or ATZ-DMDOPE incubation solution (means, n=2 determinations)

Figure 12:
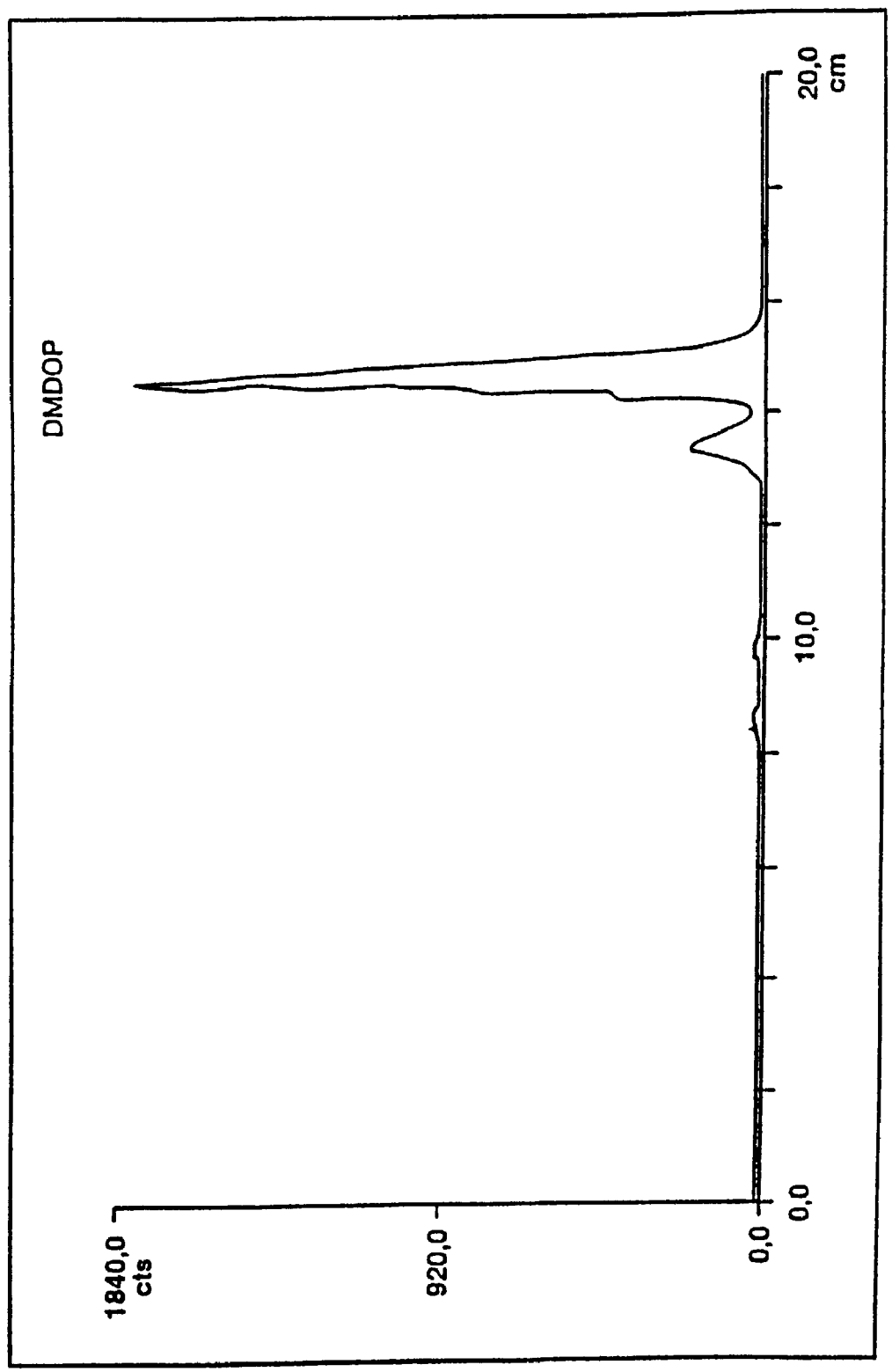

FIG. 12: Enzymatic cleavage of [$^{14}$C]-AZT-DMDOPE by membrane fractions (100 μg protein/preparation) of stimulated human PBL. Thin layer chromatogram of the n-heptane phase after adsorption of the substrate to silica gel 60H and separation in the IBA system (2-propanol:n-butyl acetate:redistilled water, 10:6:4, v/v/v) using silica gel 60 as a stationary phase.

Figure 13:
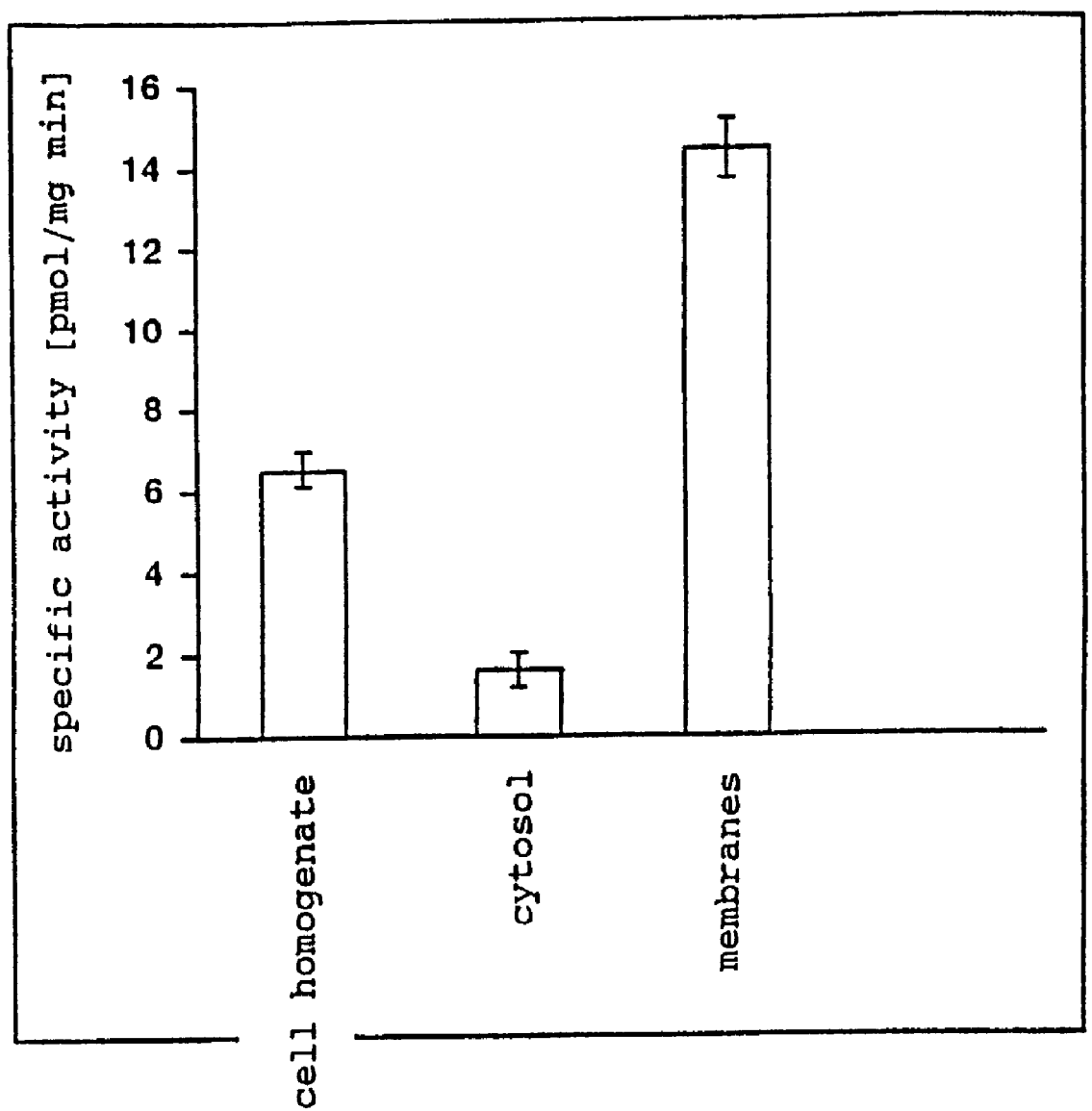

FIG. 13: Specific activity [pmol mg$^{-1}$ min$^{-1}$] of the LCE in cell homogenates, cytosol and membrane fractions of stimulated human PBL (mean±SD, n=6 determinations)

Figure 14:
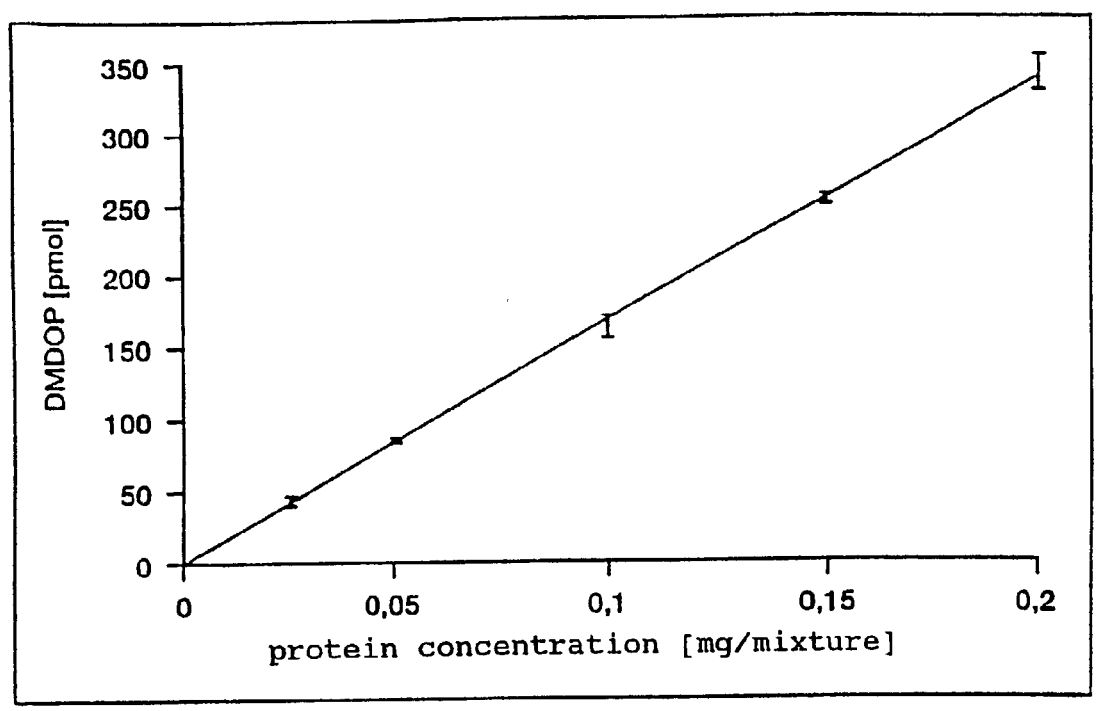

FIG. 14: Cleavage of AZT-DMDOPE by the membrane fractions of stimulated human PBL in relation to the protein concentration (mean±SD, n=3 determinations).

Figure 15:
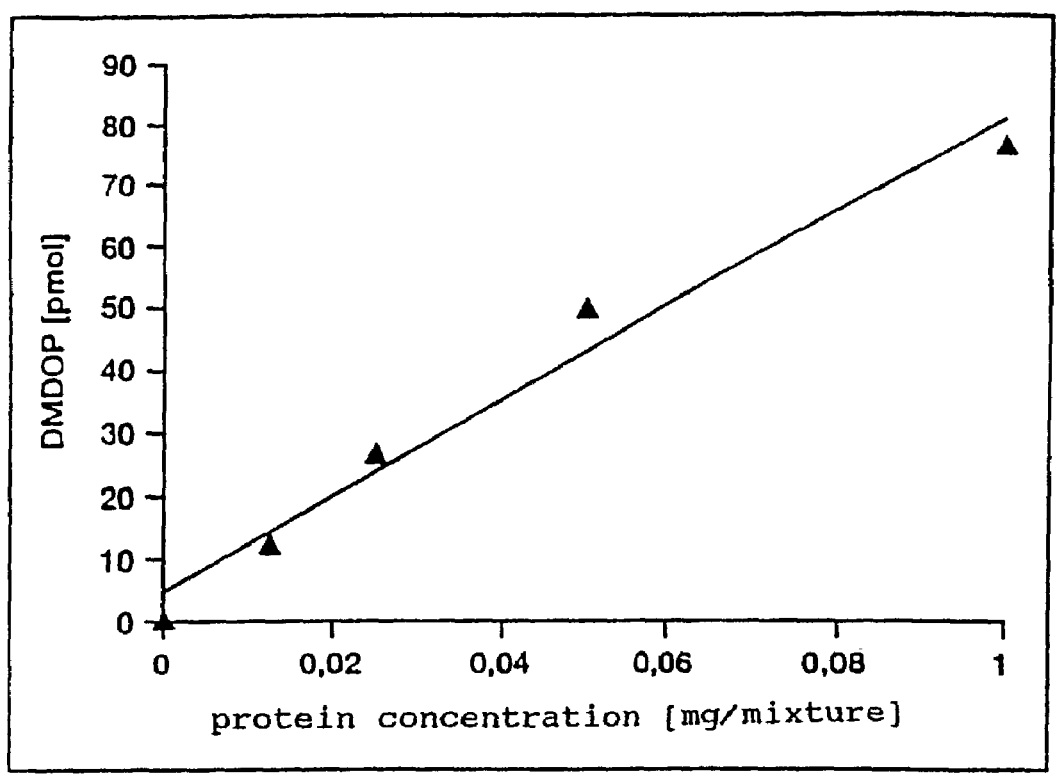

FIG. 15: Cleavage of AZT-DMDOPE by the membrane fraction of human monocytes/macrophages (stimulated monocytes) in relation to the protein concentration (mean, n=2 determinations).

Figure 16:
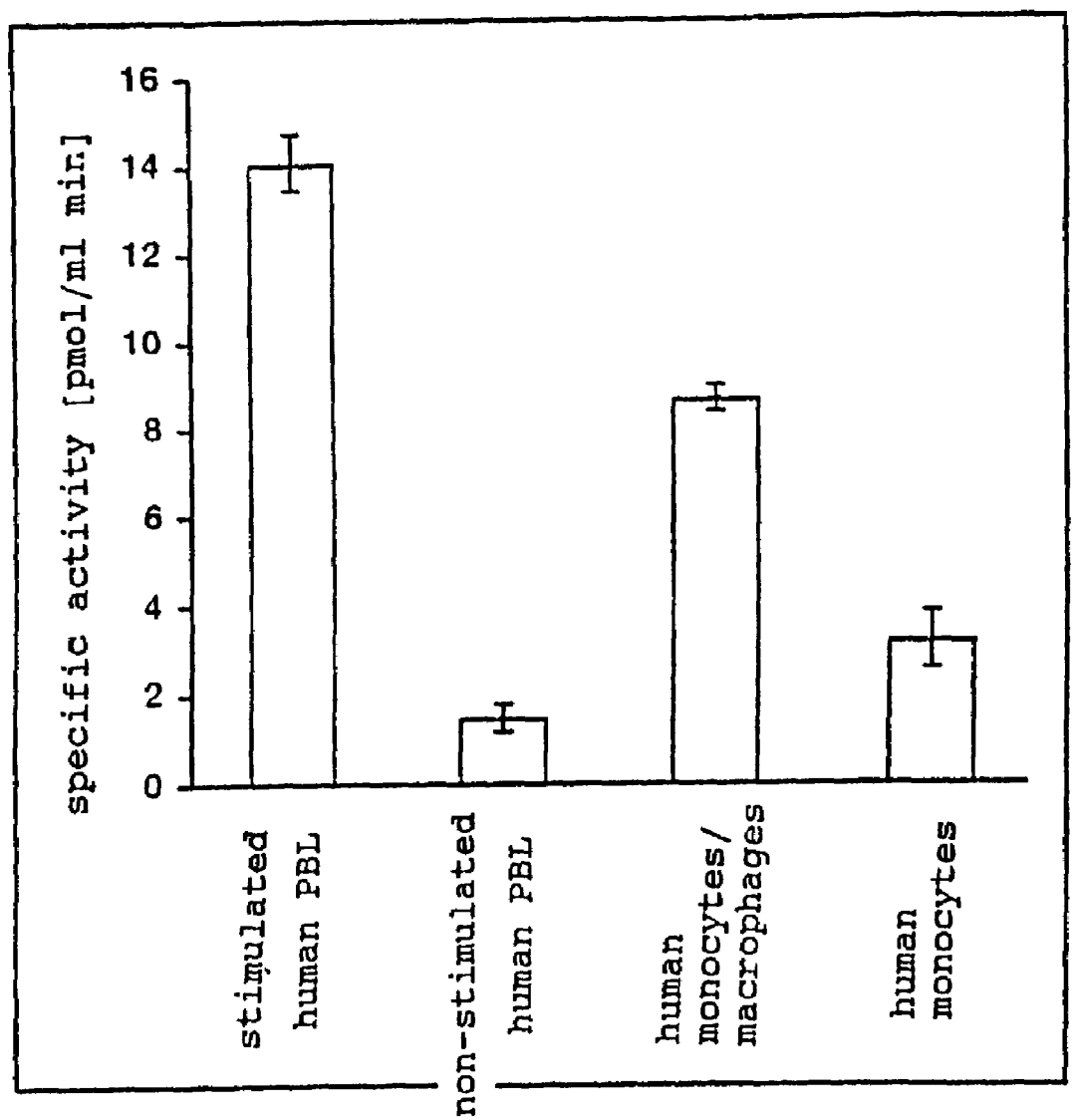

FIG. 16: Specific activity of the LCE in the membrane fractions of stimulated and non-stimulated human PBL and of human monocytes and monocytes/macrophages (stimulated monocytes) (human PBL: mean±SD, n=6 determinations) (human monocytes: mean±SD, n=4 determinations.

Figure 17:
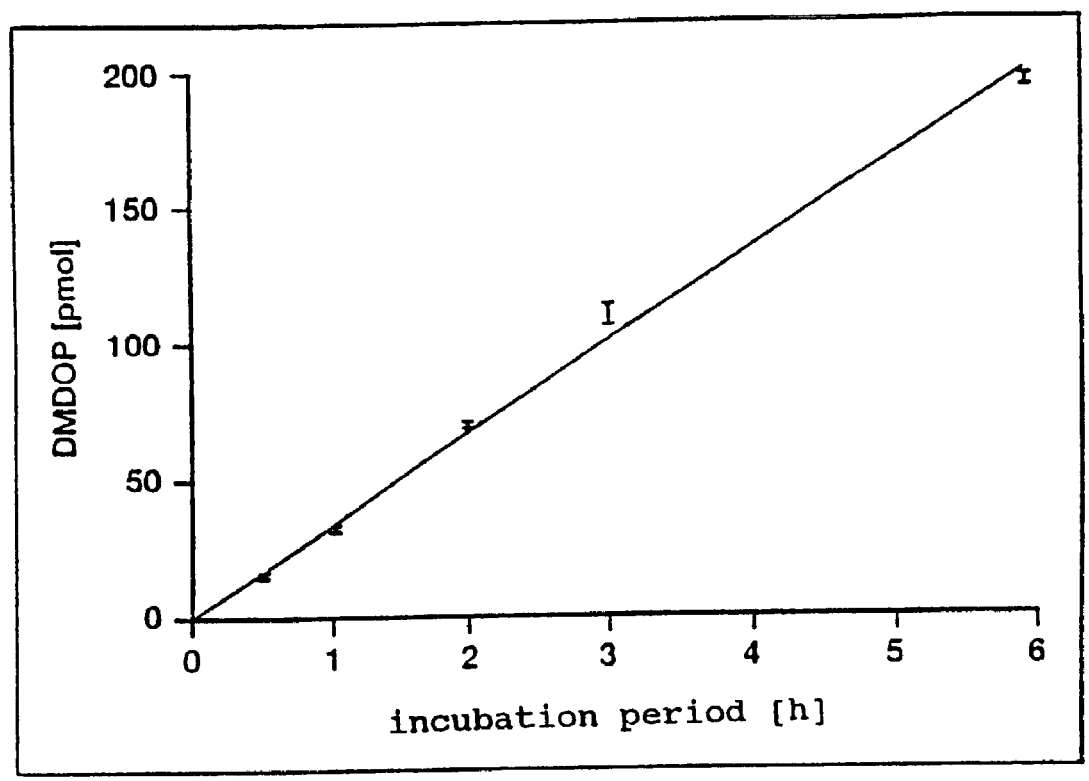

FIG. 17: Cleavage of AZT-DMDOPE by membrane fractions of stimulated human PBL in relation to the incubation time (mean±SD, n=3 determinations)

Figure 18:
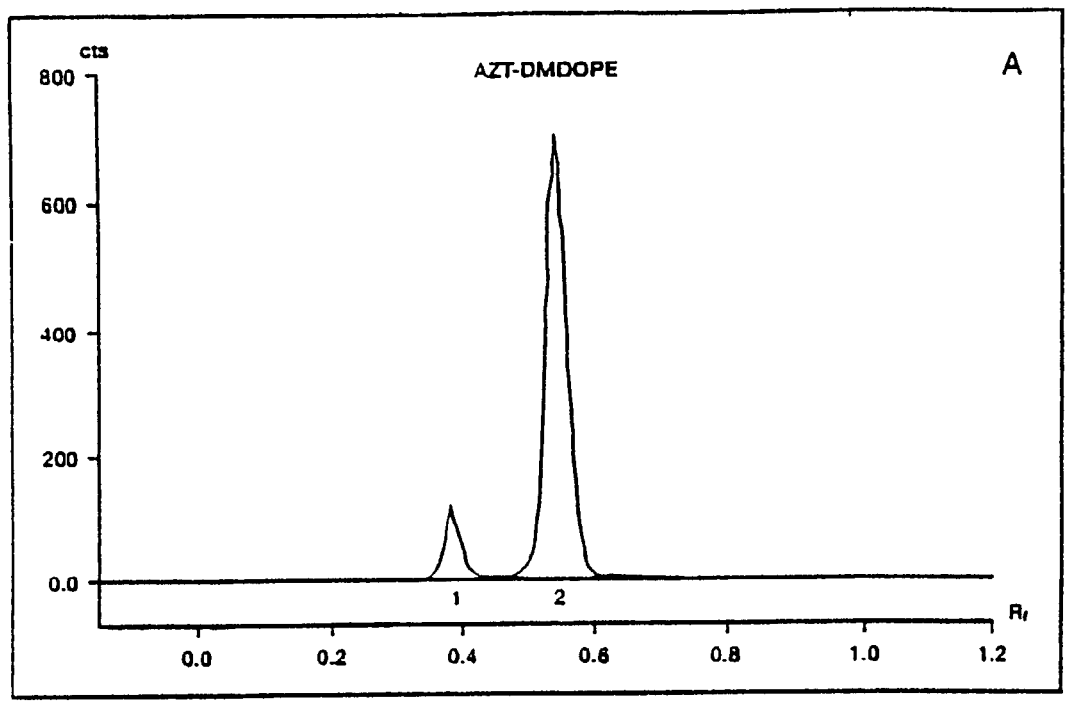
Figure 18:
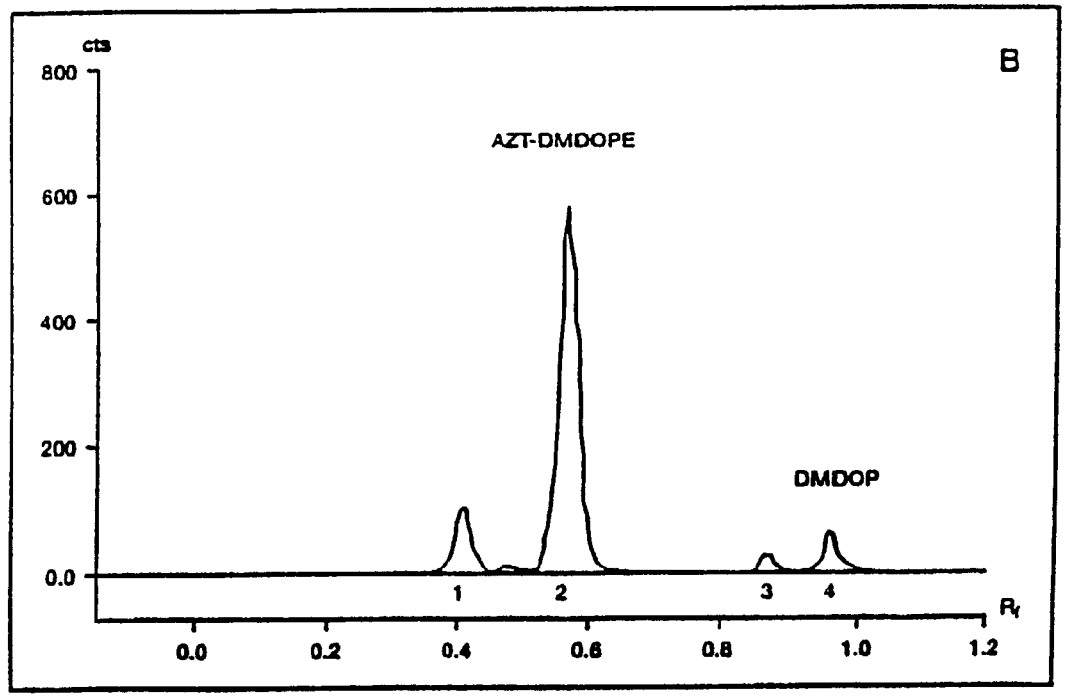

FIG. 18: Thin layer chromatogram of [$^{14}$C]-AZT-DMDOPE (A) and of [$^{14}$C]-AZT-DMDOPE after enzymatic cleavage by cell homogenates of 5×10$^7$ CEM-SS cells (B) after an incubation of 6 h at 37° C. Extraction of the thioether lipids with diethyl ether: 2 propanol (9:1, v/v) and separation in the IBAE system (2-propanol:n-butyl acetate: redistilled water:glacial acetic acid, 3:5:1:1, v/v/v/v) using silica gel 60 as a stationary phase

EXAMPLE 3

| Influence of various enzyme inhibitors or activators on the LCE activity | | | |
|---|---|---|---|
| Inhibitor/ activator | Site of attack of the inhibition/ activation | LCE membrane fraction | Influence on LCE activity |
| SQ 22536 | adenylate-cyclase | kidney (Balb/c) | none |
| 7-nitro-indazole | NO synthesis | kidney (Balb/c) | none |
| RHC-80267 | DAG lipase | kidney (Balb/c) | none |
| neomycin | PLC, (PLD) | kidney (Balb/c) | none |
| wortmannin | PLD, (PLC) | kidney (Balb/c) | none |
| acetyl-salicylic acid | PLC | kidney (Balb/c) | none |
| GTP-β-S | Gp activator | kidney (Balb/c) | none |

| Influence of various enzyme inhibitors or activators on the LCE activity | | | |
|---|---|---|---|
| Inhibitor/ activator | Site of attack of the inhibition/ activation | LCE membrane fraction | Influence on LCE activity |
| D 609 | PLC | kidney (Balb/c) CEM-SS | stimulation stimulation |

EXAMPLE 4

Subcellular Fractionation a. Preparation of Cell Homogenates, Membrane and Cytosol Fractions The cells cultured for the preparation of membrane and cytosol fractions were transferred to polypropylene tubes (50 ml) and sedimented for 10 min at 1600 rpm in a Minifuge T at room temperature. In order to remove residues of the culture medium the cell sediment was washed three times with cold PBS and taken up in lysis buffer at a cell density of 1–5×10$^8$ cells/ml. The cell suspension was subsequently transferred to a glass homogenizer cooled on ice. The cells were mechanically disrupted by several-fold movement of a teflon piston during which the cell disruption was monitored optically in a reverse phase contrast microscope. The disrupted cells were subsequently centrifuged for 10 min at 1700 rpm and 4° C. in a Minifuge T to remove the cell nuclei and the non-disrupted cells. The supernatant was carefully removed with a pipette and diluted to 10% (w/v) sucrose with 50 mM Tris buffer (pH 7.5). The cell homogenate was divided into portions and stored at −70° C. or used to isolate membrane and cytosol fractions. For this 3.2 ml of the cell homogenate was transferred to a thick-walled polycarbonate tube (3.2 ml) cooled on ice and centrifuged for 1 h at 4° C. and 75,000 rpm in a Beckmann table-top ultracentrifuge with a TLA-100.4 rotor. The supernatants were carefully removed with a Combitip pipette and the readily visible membrane sediments were each admixed with 1 ml 50 mM Tris buffer (pH 7.5)/10% sucrose. The membrane sediment was coarsely homogenized with the aid of a syringe (5 ml) with a cannula (0.9×40 mm). The coarse homogenates were combined and finely homogenized using cannulae of a smaller diameter (0.8×40 mm and 0.45×25 mm). The membrane and cytosol fractions were divided into portions and stored at −70° C.

Lysis Buffer
- 50 mM Tris pH 7.5
- 70% (w/v) sucrose
- 50 μg/ml APMSF

In order to dissolve the sucrose the buffer has to be gently warmed while stirring.

b. Isolation of the Plasma Membrane of Stimulated Human Peripheral Blood Lymnhocytes (PBL) (Record et al. (1985), Biochem. Biophys. Acta 8/9 1–9)

Human PBL were isolated by centrifugation in an isotonic density gradient and stimulated for 72 h with PHA-M. The cells were washed three times with cold PBS to remove residues of the culture medium and, after determination of the cell number, were frozen in liquid N$_2$ and subsequently stored at −70° C. The cells were lysed by freezing and thawing three times in buffer 1 whereby the cell density was adjusted to $2.5 \times 10^8$ cells/ml. A mixture of 11 ml Percoll and 2.13 ml buffer 2 was placed in Ti60 centrifuge tubes (30 ml) which had previously been adjusted to pH 9 with 70 µl 2 N NaOH. For the isolation of the plasma membrane 4 ml of the homogenate was applied to the mixture and subsequently centrifuged for 10 min at 4° C. and 39,000 rpm in a Ti60 rotor of a Beckmann ultracentrifuge L 5 50 with the brake switched off. 1 ml fractions were taken from the upper phase of the centrifuge tubes and diluted with 2 ml buffer 3. The solutions were subsequently transferred to Ti50 tubes (10.4 ml) and centrifuged for 45 min at 4° C. and 45,000 rpm in a Beckmann ultracentrifuge L 5 50 with a Ti50 rotor to remove residues of the separation medium. The supernatants were removed with a pipette, fractionated, frozen in liquid $N_2$ and stored at −70° C. The fractions were characterized by determining the protein content and the enzyme activity of alkaline phosphatase.

| Buffer 1 | 100 mM | KCl |
| --- | --- | --- |
| | 5 mM | $MgCl_2 \cdot x6H_2O$ |
| | 1 mM | ATP |
| | 2 mM | (4-amedinophenyl)-methane sulfonylfluoride (APMSF) |
| | 25 mM | Tris pH 9.6 |
| Buffer 2 | 400 mM | KCl |
| | 20 mM | $MgCl_2 \cdot xH_2O$ |
| | 400 mM | Tris pH 9.6 |
| Buffer 3 | 100 mM | KCl |
| | 5 mM | $MgCl_2 \cdot x6H_2O$ |
| | 50 mM | Tris pH 7.42 |

EXAMPLE 5

Production of Substrate Solutions for the LCE Assay

A mixture of [$^{14}C$]-AZT-DMDOPE and non-radioactively labelled AZT-DMDOPE was used as a substrate in the LCE assay.

Starting with a [$^{14}C$]-AZT-DMDOPE stock solution, a solution with a specific activity of 83.27 kBq/ml was prepared by dilution with ethanol. The ethanolic solution could be stored for 2 months at 4° C. under inert gas.

In a separate mixture the non-radioactively labelled component of the substance mixture was prepared. For this a solution of AZT-DMDOPE at a concentration of 1 µmol/ml in ethanol was prepared and continuously sonicated at 30% energy release for 1 min in an ice/water bath with an ultrasonic probe.

In order to prepare the substrate mixture of radioactive and non-radioactive AZT-DMDOPE, 1.67 kBq of the radioactively labelled [$^{14}C$]-AZT-DMDOPE and 0.7–5 nmol of the non-labelled compound were transferred per mixture from these ethanolic solutions into a glass tube (10 ml). The solvent was evaporated in a $N_2$ stream and AZT-DMDOPE was taken up in a suitable volume of redistilled water and continuously sonicated at 30% energy release for 1 min while cooling in an ice/water bath.

EXAMPLE 6

Lipid Cleavage Enzyme (LCE) Assay

In order to examine the enzymatic cleavage relative to time and the protein concentration 5 nmol AZT-DMDOPE and 0.98 nmol [$^{14}C$]-AZT-DMDOPE (1.67 kBq) In a volume of 200 µl redistilled water were usually used in the LCE assay. The pipetting scheme is given in the following table.

TABLE

Pipetting scheme for the LCE assay to determine the turnover of AZT-DMDOPE

| | Reaction mixture | Control |
| --- | --- | --- |
| EGTA [20 mM] | 50 | 50 |
| Tris, pH: 8.0 [1 M] [µl/mixture] | 50 | 50 |
| AZT-DMDOPE/[$^{14}C$]-AZT-DMDOPE [nmol/mixture] | 0.10–5.98 | 0.10–5.98 |
| [µl/mixture] Protein | 5–200 | 5–200 |
| [mg/mixture] | 0.0125–0.2 | — |
| [µl/mixture] | x | — |
| redistilled water [µl] | ad 500 | ad 500 |

In order to examine the enzymatic cleavage in relation to the substrate concentration, a substrate stock solution of 0.98 nmol [$^{14}C$]-AZT-DMDOPE and 0.7 nmol AZT-DMDOPE/80 µl redistilled water was used in the LCE assay. The various substrate concentrations were adjusted in the LCE assay by continuously doubling or halving the volume of the substrate solution. The mixtures were placed in glass tubes (5 ml) and started by adding the substrate solution. The incubation was carried out at 37° C. in a water bath while gently shaking.

EXAMPLE 7

Extraction of DMDOP from an Aqueous Matrix

The reaction mixtures of the LCE assays were taken from the water bath after an appropriate incubation period and the reaction was stopped by adding 750 µl 2-propanol.

After thorough mixing 700 µl n-heptane heated to room temperature was added to the mixtures. The mixtures were again thoroughly mixed for 30 sec and centrifuged for 15 min in a Minifuge T at 3200 rpm at room temperature to accelerate the phase separation. Subsequently 500 µl of the upper phase (n-heptane) was removed and transferred to new glass tubes (5 ml) containing 10 mg silica gel 60 H and 200 µl n-heptane. The mixtures were thoroughly mixed for 30 sec and centrifuged for 10 min under the conditions mentioned above to sediment the silica gel. Subsequently 500 µl was taken from the supernatant and admixed with 3 ml scintillation liquid. The radioactivity was measured for 4 min in a liquid scintillation analyzer. In order to determine the absolute value of radioactivity, 200 µl of the substrate solution was mixed with 3 ml scintillation liquid and measured under the same conditions in the liquid scintillation analyzer.

EXAMPLE 8

In Vitro Pharmakokinetic Studies with AZT-DMDOPE and AZT a) Determination of the Intracellular Concentrations of AZT and/or AZT Nucleotides in Stimulated and Non-stimulated Human PBL After Incubation with AZT-DMDOPE and AZT.

Human PBL were isolated from the buffy coat in order to determine the intracellular concentrations of AZT and/or AZT nucleotides after incubation with AZT-DMDOPE and AZT.

For this the buffy coat of healthy donors is mixed and fractionated by centrifugation in an isotonic medium with a density of 1.077 g/ml. Since mono-nuclear blood cells (monocytes and lymphocytes) have a lower density than erythrocytes and polymorphonuclear granulocytes they form a ring at the border between the separation medium and the sample and can be removed with the aid of a pipette. Erythrocytes and polymorphonuclear granulocytes sediment through the medium as a result of their higher density and can thus be separated from the PBLs.

In order to stimulate cell proliferation phytohaemagglutinin A (mucoprotein) (PHA-M) the mitogenic lectin extract from the red scarlet runner (Phaseolus vulgaris) was used. Phytohaemagglutinin is a family of 5 isolectins which are present as tetramers. The subunits are composed of a lymphocyte-reactive type L and an erythrocyte-reactive type E. Type L has a high affinity to lymphocyte surface receptors and is thus responsible for the mitogenic properties. The lymphocytes were stimulated for 72 h at 37° C. and 5% $CO_2$ in KPMI 1640 complete medium III. After the stimulation was complete the cells were cultured for a further 24 h in RPMI 1640 complete medium IV to increase the cell number.

For the determination of the intracellular concentrations of AZT and AZT nucleotides the cells were transferred into RPMI 1640 complete medium II at a density of $1 \times 10^6$ cells/ml in tissue culture flasks (50 ml/25 cm$^2$) and incubated for 1 to 24 h in the presence of 0.03 and 0.3 μg AZT/ml (lot 15) and 1 or 10 μg AZT-DMDOPE/ml.

The concentrations of AZT-DMDOPE and AZT in this case depend on the IC50 values for the antiretroviral activity which was determined for AZT and AZT-DMDOPE in HIV-1 infected human PBL.

The cultures were subsequently incubated for 1, 3, 6 and 24 h at 37° C. and 5% $CO_2$. AZT and its nucleotides were subsequently extracted with 60% methanol. The extracted nucleotides were quantitatively dephosphorylated to AZT with alkaline phosphatase since only AZT but not the corresponding nucleotides can be detected with the aid of a radioimmunoassay.

Accordingly the concentrations of intracellular AZT that were determined with the aid of a radioimmuno-assay were composed of that of the AZT and that of the AZT nucleotides together. A separate quantification of the concentrations of AZT-MP, AZT-DP and AZT-TP was not carried out. Experimental observations on stimulated PBL were able to demonstrate a 40-fold higher concentration of AZT-MP compared to AZT-DP and AZT-TP (Arner et al., 1992, J. Biol. Chem. 267, 10968–10975). Consequently it can be assumed that the nucleotide fraction is almost exclusively composed of AZT-MP.

In stimulated human PBL a maximum concentrations of 2.90 and 30.97 ng/10$^6$ cells was reached after an incubation of 6 and 3 h respectively when incubated with 0.03 and 0.3 μg AZT/ml respectively (FIG. 6). The concentrations subsequently decreased as the incubation period increased to 2.32 and 19.88 ng/10$^6$ cells respectively. After incubation with 1 and 10 μg AZT-DMDOPE/ml there was a continuous increase in the intracellular level of AZT and its nucleotides over the entire incubation period. After 24 h incubation with AZT-DMDOPE and AZT the intracellular levels were identical. In further experiments it was possible to show that the intracellular concentrations of AZT and AZT nucleotides after incubation with AZT-DMDOPE for a period of 18–48 h was even higher than after incubation with an equipotent concentration of AZT.

In the case of non-stimulated human PBL the opposite relationships were found (FIG. 7). Thus after incubation with AZT-DMDOPE the intracellular concentrations of AZT and AZT nucleotides were higher than after incubation with an equipotent concentration of AZT over the entire incubation period. After incubation with 1 and 10 μg AZT-DM-DOP/ml maximum intracellular concentrations of AZT and AZT nucleotides of 0.62 and 4.74 ng/10$^6$ cells respectively were reached whereas after incubation with 0.03 and 0.3 μg AZT/ml concentrations of 0.10 and 0.47 ng/10$^6$ cells respectively were detected.

In order to separately quantify AZT and AZT nucleotides after incubation with BM 21.1290 Na all intracellular concentrations of AZT and AZT nucleotides were determined with and without treatment with alkaline phosphatase. These experiments were carried out on stimulated human PBL.

For this cell suspensions with a density of 10$^6$ cells/ml containing 1 and 10 μg AZT-DMDOPE/ml were incubated for 6 and 24 h at 37° C. and 5% $CO_2$. The maximum intracellular concentrations of free AZT after incubation with 1 and 10 μg AZT-DMDOPE/ml were detected as 0.03 and 0.15 ng/10$^6$ cells respectively after 6 and 24 h respectively (FIG. 8). If after treatment with alkaline phosphatase the phosphorylated intracellular AZT nucleotides were additionally measured then maximum concentrations of 3.85 and 6.41 ng/10$^6$ cells respectively were found after 24 h.

b. Determination of the Intracellular Concentrations of AZT and/or AZT Nucleotides in P3X63Ag8.653 Cells After Incubation with AZT-DMDOPE and AZT The determination of the intracellular concentrations of AZT and AZT nucleotides in thymidine kinase deficient cells should yield more information about the intracellular cleavage of the test substance AZT-DMDOPE. Intracellular AZT cannot be converted into AZT-MP and thus into the therapeutically effective AZT-TP due to a lack of thymidine kinase (TK) in these cells. The determination of the intracellular concentrations of AZT and AZT nucleotides after incubation with AZT-DMDOPE could thus give a further information on the cleavage of the test substance.

For this $1 \times 10^7$ cells in RPMI 1640 complete medium I containing 0.03 or 0.3 μg AZT/ml and 1 or 10 μg AZT-DMDOPE/ml were incubated for 6, 24 and 48 h in tissue culture plates (60×15 mm). After extracting the AZT and AZT nucleotides and treatment with alkaline phosphatase the concentration of AZT was determined with the aid of the radioimmunoassay.

The graphical plot of the experimental results shows that the intracellular concentrations of AZT and AZT nucleotides were considerably higher with AZT-DMDOPE than after incubation with equipotent concentrations of AZT. Thus after 6 h incubation with 1 and 10 μg AZT-DMDOPE/ml maximum concentrations of AZT and AZT nucleotides of 0.55 and 4.40 ng/10$^6$ cells respectively were achieved (FIG. 9).

The maximum intracellular concentrations of AZT and AZT nucleotides after incubation with 0.03 and 0.3 μg AZT/ml were determined as 0.03 and 0.31 ng/10$^6$ cells respectively.

In order to quantify the proportion of phosphorylated AZT the intracellular concentrations of AZT and AZT nucleotides were compared before and after treatment of the cellular extracts with alkaline phosphatase. The substance level of phosphorylated AZT after incubation with 1 and 10 μg AZT-DMDOPE/ml yielded values in this case of 0.48 and 2.42 ng/10$^6$ cells respectively (FIG. 10). If only AZT was measured then maximum concentrations of 0.05 and 1.10 ng/ml respectively were reached after 24 h. The differences in the intracellular concentrations of AZT nucleotides after incubation with AZT and AZT-DMDOPE can be explained by an intracellular cleavage of the test substance AZT-DMDOPE to AZT-MP.

c. Kinetics of the Decrease of AZT and AZT Nucleotides in Stimulated Human PBL after Incubation with AZT-DMDOPE and AZT Stimulated human PBL were incubated for 24 h with 0.3 µg AZT/ml or 10 µg AZT-DMDOPE/ml. Subsequently $1 \times 10^7$ cells were transferred into tissue culture flasks (50 ml/25 cm$^2$) containing RPMI 1640 complete medium I. After 1, 3, 6, 24 and 48 h AZT and AZT nucleotides were extracted from the cellular matrix. After treatment with alkaline phosphatase the concentration of AZT was determined with the aid of a radioimmunoassay.

The graphic representation of the experimental results shows that after incubating the cells with AZT the intracellular concentrations of AZT and AZT nucleotides decrease rapidly and reach a constant value of 0.40 ng/10$^6$ cells after 6 h. In contrast in the incubation with an equipotent concentration of AZT-DMDOPE the AZT and AZT nucleotides decrease less rapidly and after 3 h reach a substantially higher concentration of 1.80 ng/10$^6$ cells which remains constant over 48 h (FIG. 11). Since non-phosphorylated AZT was removed from the cell by washing several times with PBS, the intracellular concentrations are mainly attributable to phosphorylated AZT nucleotides. Thus an incubation with AZT-DMDOPE provides the cell with a 4.5-fold higher concentration of phosphorylated AZT compared to an equipotent concentration of AZT. These large differences in the cellular concentrations of AZT nucleotides after incubation with AZT-DMDOPE and AZT can be explained by a direct intracellular cleavage of the thioether-lipid-AZT conjugate AZT-DMDOPE to AZT-MP and the corresponding thioether lipid moeity DMDOP.

EXAMPLE 9

Characterization of the AZT-DMDOPE Cleavage Enzyme/Enzyme System (LCE)

Investigations on the enzymatic cleavage of AZT-DMDOPE by cell homogenates of human PBL and CEM-SS cells showed that AZT-DMDOPE is metabolized to DMDOP and AZT-MP. The characterization of the LCE was the object of the following investigations. Thus the dependency of the enzymatic cleavage of AZT-DMDOPE on the protein concentration, the incubation period and divalent metal cations was examined. The dependency of the apparent Michaelis-Menten parameters $K_M$ and $v_{max}$ on various substrate concentrations is determined in enzyme kinetic experiments.

For these experiments an enzyme assay is established in which AZT-DMDOPE and [$^{14}$C]-AZT-DMDOPE were used as the substrate (example 6). In protein and time dependent measurements 5 nmol AZT-DMDOPE and 0.98 nmol (1.67 kBq) [$^{14}$C]-AZT-DMDOPE were used per mixture. In the case of substrate-dependent conversions a stock solution of 0.98 nmol [$^{14}$C]-AZT-DMDOPE and 0.7 nmol AZT-DMDOPE/80 µl was used. The various substrate concentrations were subsequently adjusted by continuously doubling or halving the volume of the substrate solution.

Cell homogenates, cytosol and membrane fractions of known protein concentrations from various human cells can for example be used as the enzyme source.

a. Isolation and Quantification of DMDOP After Enzymatic Cleavage of AZT-DMDOPE

The quantification of the enzymatic cleavage of AZT-DMDOPE was carried out by two-step extraction of the metabolite DMDOP with n-heptane and subsequent adsorption of residues of the substrate AZT-DMDOPE on silica gel 60 H.

For this the reaction mixtures were admixed with 2-propanol and n-heptane in the process of which the DMDOP which is less polar than the substrate accumulates in the n-heptane phase. The n-heptane phase was then admixed with silica gel 60H which adsorbs residues of the substrate AZT-DMDOPE. The n-heptane phase was afterwards separated from the silica gel by centrifugation, transferred to 3 ml aqua luma and the amount of radioactively labelled DMDOP contained therein was determined over a period of 5 min in a liquid scintillation analyzer. From these results it was possible to calculate the percentage conversion of the substrate AZT-DMDOPE to DMDOP and the specific activity of the LCE. In this case the specific activity is defined as the amount of DMDOP which is formed per minute per 1 mg protein of the cell preparations used.

In order to check the selective extraction of DMDOP from the reaction mixture, optimization experiments were carried out with membrane fractions of stimulated human PBL. In this case the protein concentration was 100 µg/mixture. Mixtures without protein were tested in parallel. After the extraction the n-heptane phase was evaporated in an N$_2$ stream and the residues were taken up in a mixture of methanol and ethyl acetate (1:1, v/v).

The analysis by thin layer chromatography was carried out in the IBA system. The reaction value in this case only allowed the parent substance [$^{14}$C]-AZT-DMDOPE to be detected. In the reaction mixture a substance peak was detected at the end of the mobile solvent front which could be identified unequivocally as the metabolite [$^{14}$C]-DMDOPE on the basis of its $R_f$ value (FIG. 12). The peak which runs immediately in front of the DMDOP substance peak cannot be allocated to either of the known compounds. It is presumably a compound which is formed by oxidation of the sulphur in the thioether lipid moeity of DMDOP. Hence an extraction with n-heptane enables the enzymatic cleavage product DMDOP to be isolated from the enzyme assay. A simple and rapid quantification of the metabolite DMDOP released from AZT-DMDOPE was thus ensured.

b. Cleavage of AZT-DMDOPE by Cell Homogenates, Membrane and Cytosol Fractions of Stimulated Human PBL In a first series of experiments the enzymatic cleavage of AZT-DMDOPE by cell homogenates and by cytosol and membrane fractions of stimulated human PBL was examined.

After determining the protein concentration in cell homogenates, cytosol and membrane fractions with the aid of the bicinchoninic acid (BCS) test 0.025–0.20 mg protein/mixture were used. The reaction mixtures were incubated for 2 h at 37° C., subsequently the product DMDOP was isolated from the mixtures by extraction with n-heptane and the specific activity of the LCE was determined (FIG. 13).

The AZT-DMDOPE-cleaving activity in cell homogenates and in cytosol fractions of 6.48±0.38 (n=6) and 1.65±0.40 pmol mg$^{-1}$ min$^{-1}$ (n=6) was 1.59-fold and 6.3-fold smaller than the specific activity in the membrane fractions which was 14.23±0.70 (n=6) pmol mg$^{-1}$ min$^{-1}$. Apparently there is an enrichment of the LCE when the membrane fractions are isolated. Based on these results membrane fractions were used in the subsequent experiments for determining the enzymatic parameters of the LCE.

The membrane fraction which was obtained by mechanically disrupting the cells and subsequent ultracentrifugation of the cell homogenate is a mixture of fragments of the plasma membrane and nuclear membrane as well as membranes of the cell organelles.

It was possible to differentiate the various membrane fragments by ultracentrifugation of the cell homogenate in Percoll density gradients followed by a subsequent characterization by the plasma membrane marker alkaline phosphatase.

For the isolation of the plasma membranes 2 ml of a cell suspension of stimulated human PBL with a cell density of $2.5 \times 10^8$ cells/ml was disrupted by freezing and thawing three times and fractionated by centrifugation in a Percoll density gradient. 10 fractions (1 ml) were taken from the centrifugate, residues of the separating medium were removed and the activity of alkaline phosphatase in the individual fractions was measured at 305 nm using p-nitrophenylphosphate as the substrate.

The highest activity of alkaline phosphatase was determined in fraction 8. The absorbance of the remaining fractions was much less. This indicates an enrichment of the plasma membranes in fraction 8. The specific LCE activity was determined in each fraction after determining the protein concentration. For this the protein concentration was adjusted to 0.05 mg/mixture and the reaction mixtures were incubated for 2 h at 37° C., The highest specific LCE activity of 4.40 pmol $mg^{-1}$ $min^{-1}$ was determined in this case in fraction 8.

In all other fractions lower specific activities of 1.10–1.90 pmol $mg^{-1}$ $min^{-1}$ were measured (FIG. 4.32). The highest specific activity of LCE was thus determined in the fraction which at the same time had the highest activity of alkaline phosphatase. Hence this finding shows that LCE occurs in the fraction with the highest amount of fragments of the plasma membrane.

c. Dependency of the Specific LCE Activity on the Protein Concentration

In further investigations it was intended to determine the dependency of the turnover of AZT-DMDOPE on increasing protein concentrations of the cell preparations.

For this membrane fractions of stimulated and non-stimulated human PBL and of human blood monocytes were used. The conversion of AZT-DMDOPE to DMDOP by the membrane fractions of stimulated human PBL exhibited a linear behaviour when using 0.025–0.2 mg protein/mixture (FIG. 14). The specific LCE activity was 14.23±0.7 pmol $mg^{-1}$ $min^{-1}$ (n=6) (FIG. 16). When AZT-DMDOPE was converted by proteins of the membrane fraction of non-stimulated human PBL there was a linear relationship only in the concentration range up to 0.05 mg protein/mixture. At higher protein concentrations there was no longer a linearity. The specific LCE activity which was calculated from the turnovers in the linear range was 1.45±0.32 pmol $mg^{-1}$ $min^{-1}$ (n=6).

In order to determine the specific LCE activity in human blood monocytes these were isolated in hypertonic density gradients. Monocytes have a density of 1.068 g/ml on average which is somewhat lower than that of lymphocytes with 1.070 g/ml. This difference in the density is however, very small so that it is not possible to separate these blood cells in an isotonic gradient.

Under hypertonic conditions lymphocytes lose water more rapidly than monocytes resulting in an increase in their density. Hence it is possible in a hypertonic separating medium to isolate monocytes from whole blood or leucocyte rich plasma. It is also possible to isolate human blood monocytes from buffy coat. For this mononuclear cells are separated under isotonic conditions in a density gradient and monocytes are subsequently separated in tissue culture flasks (175 $cm^2$/800 ml) on the basis of their adherence.

With the aid of flow cytofluorometric analysis it was possible to detect a stimulation of these cells by adherence after determination of size and granularity as well as after specific antibody staining. As a result of this stimulation the monocytes which were isolated by adherence to the bottom of tissue culture bottles were denoted monocytes/macrophages (stimulated monocytes) in the following.

In the enzymatic turnover of AZT-DMDOPE by the membrane fraction of human monocytes which had been stimulated during the course of their isolation by adherence, a linear dependency was found up to a concentration of 0.1 mg protein/mixture (FIG. 15). The specific activity was 8.8±0.26 pmol $mg^{-1}$ $min^{-1}$ (n=4) (FIG. 16). When the monocytes were isolated directly in a hypertonic density gradient then there was a linear behaviour of the enzymatic cleavage only up to a protein concentration of 0.025 mg protein/mixture. At higher protein concentrations the substrate turnover was almost constant. The specific activity was calculated from the linear range analogously to the turnover with the membrane fractions of non-stimulated human PBL and was 3.2+0.60 pmol $mg^{-1}$ $min^{-1}$ (n=4).

In summary it was established that higher specific LCE activities were observed when AZT-DMDOPE was converted by enzymes of the membrane fractions of stimulated human PBL and monocytes than when AZT-DMDOPE was converted by membrane fractions of non-stimulated cells (FIG. 16).

d. Dependency of the Specific LCE Activity on the Incubation Period

The enzymatic cleavage of the experimental substance AZT-DMDOPE in relation to the incubation period was carried out with membrane fractions of stimulated human PBL as the enzyme source. The reactions mixtures were incubated for 0.5, 1, 2, 3 and 6 h at 37° C. and subsequently the amount of the metabolite DMDOP was determined. After plotting the experimental results on a graph it was possible to show that the conversion of AZT-DMDOPE to DMDOP is linear over the entire period of incubation of 0.5–6 h (FIG. 17).

e. Dependency of the Specific LCE Activity on Divalent Metal Cations

The dependency of the enzymatic cleavage of AZT-DMDOPE by LCE on divalent metal cations was examined with membrane fractions of stimulated human PBL as the enzyme source.

The divalent metal cations were used at a concentration of 2 mM in the LCE assay. The protein concentration was fixed at 0.068 mg/mixture.

An experiment with EGTA was carried out in parallel. EGTA is a specific complexing agent for $Ca^{2+}$ which is essential for the activity of phospholipase C. After an incubation time of 2 h at 37° C. the conversion of the parent substance was measured and the specific activity of the LCE was determined (following table).

TABLE

Dependence of the cleavage of AZT-DMDOPE by
membrane fractions of stimulated human PBL
on EGTA and divalent metal cations (mean ±
SD, n = 3 determinations)

| Effector [2 mM] | DMDOP [pmol] | Specific activity [pmol mg$^{-1}$ min$^{-1}$] | Inhibition [%] |
|---|---|---|---|
| EGTA | 84.96 ± 11.18 | 10.41 ± 1.37 | ≡0 |
| CaCl$_2$ | 50.50 ± 2.13 | 6.19 ± 0.26 | 41.0 ± 2.5 |
| MgCl$_2$ | 84.36 ± 17.02 | 10.34 ± 2.08 | 0 |
| ZnCl$_2$ | 0 | 0 | 100.0 |
| MnCl$_2$ | 4.75 ± 0.63 | 0.58 ± 0.08 | 94 ± 1 |

The highest specific activity achieved when using EGTA and MgCl$_2$ was 10.41±1.37 (n=3) and 10.34±2.08 pmol mg$^{-1}$ min$^{-1}$ (n=3) respectively. Thus it was not possible to detect any inhibition by MgCl$_2$ within the limits of the measurement accuracy. When CaCl$_2$ was used in the enzyme assay a specific activity of 6.19±0.26 pmol mg$^{-1}$ min$^{-1}$ (n=3) was determined. In comparison with the mixture containing EGTA this means an inhibition of the LCE activity of 41.0±0.25% (n=3). In the case of ZnCl$_2$ no DMDOP was detectable within the limits of the measurement accuracy. ZnCl$_2$ and MgCl$_2$ led to a total inhibition of the conversion of AZT-DMDOPE to DMDOP and AZT-MP.

f. Determination of the Apparent Michaelis-Menten Parameters $K_M$ and $v_{max}$ In order to determine the apparent Michaelis-Menten parameters for the LCE the dependence of the enzymatic cleavage of AZT-DMDOPE on increasing substrate concentrations was examined.

TABLE

Apparent Michaelis-Menten parameters $K_M$ and $v_{max}$
of the LCE in stimulated and non-stimulated human
PBL and in human monocytes and monocytes/
macrophages (stimulated monocytes)

| | $v_{max}$ [pmol mg$^{-1}$ min$^{-1}$] | $K_M$ [µM] |
|---|---|---|
| non-stimulated PBL | 2.03 ± 0.19 | 5.51 ± 0.99 |
| stimulated human PBL | 15.29 ± 0.37 | 2.26 ± 0.16 |
| human monocytes | 1.61 ± 0.37 | 12.08 ± 4.13 |
| human monocytes/macrophages (stimulated monocytes) | 0.09 ± 0.44 | 4.63 ± 0.45 |

For this membrane fractions of stimulated and non-stimulated human PBL as well as human monocytes and monocytes/macrophages (stimulated monocytes) were used. The reaction mixtures contained a constant protein amount of 0.068 mg/mixture and were incubated for 2 h at 37° C. Subsequently the amount of the metabolite DMDOP was determined.

EXAMPLE 10

Experimental Animals

In order to determine the pharmakokinetic parameters of the experimental substance AZT-DMDOPE, in vivo experiments were carried out on female Balb/c mice (Charles River Wiga, Sulzfeld; Bormholtgard, Ry (Denmark); Iffa Credo, L'Abresle (France)). The animal deliveries were examined before the experiment started for virus antibodies (mice hepatitis virus, reo virus, paro virus). In the experiments only animals were used which had a negative antibody titre.

Keeping the Experimental Animals

The animals were kept in fully air-conditioned animal cages at a room temperature of 22–24° C., a relative air humidity of 50–70% and a day-night rhythm of 12 hours. Laminar flow boxes ensured that the air in the animal cage was exchanged 15–20 times per hour. The animals were administered a standard diet (Ssniff, Soest) and water ad libitum via a drinking bottle.

Example 11

Cell Culture Methods a. Cryonreservation of Cell Lines

For the cryopreservation, cells were adjusted to a cell density of 5×10$^6$ cells/ml in RPMI 1640 medium and sedimented for 10 min at 1600 rpm in a Minifuge T. Subsequently the cell sediment was taken up in an equal volume of cryopreservation medium. After resuspension of the cell sediment 1 ml of the cell suspension was transferred in each case to cryo-tubes (1.8 ml) and frozen for 24 h at −70° C. The cryo tubes were transferred to a thermo-container containing liquid N$_2$ for the final storage.

Cryopreservation 60% (v/v) RPMI 1640 medium
medium 0.05 mM 2-mercaptoethanol
    100 U/ml penicillin
    100 µg/ml streptomycin
    30% (v/v) foetal calf serum
    10% (v/v) DMSO b. Type Culturing and Growth Conditions Culturing of CEM-SS Cells The suspension cell line CEM-SS was cultured in RPMI 1640 complete medium I. For this 1×10$^7$ cells were transferred to a tissue culture flask (83 cm$^2$/260 ml) containing 50 ml medium. Subsequently the culture was incubated for 3 days at 37° C. and 5% CO$_2$. For the cell passage the cells were removed from the tissue culture flask with a sterile pipette and sedimented for 10 min at 1600 rpm in a Minifuge T. After resuspending the cells in culture medium and determining the cell number by eosin staining in a Neubauer counting chamber, 1×10$^7$ cells were used for passage into 50 ml fresh medium.

Culture of P3X63Ag8.653 Cells

P3X63Ag8.653 cells were cultured as a monolayer in RPMI 1640 complete medium I. For this 5×10$^6$ cells were transferred to a tissue culture flask (83 cm$^2$/260 ml) containing 40 ml medium. The cell culture was incubated for 5 days at 37° C. and 5% CO$_2$ until the bottom of the tissue culture flask was covered with a confluent cell monolayer. For the cell passage the adherent cells were mechanically detached from the bottom of the flask using a cell scraper and subsequently sedimented by centrifugation for 10 min at 1600 rpm in a Minifuge T. After resuspending the cells in culture medium the cell number was determined by eosin staining in a Neubauer counting chamber and 5×10$^6$ cells were used for passage into 40 ml fresh medium.

c. Determining the Cell Count

Determination of the Cell Count by Eosin Staining in a Neubauer Counting Chamber (Lindl and Bauer, 1989, "Zell und Gewebekultur", P. 75–90, Gustav Fisher Verlag, Stuttgart, N.Y.)

For the determination of the cell count in suspension and monolayer cultures a cell concentration of $0.1-1\times10^6$ cells/ml was adjusted in PBS and a portion of this cell suspension was admixed with 20 µl eosin. Subsequently the cell suspension was carefully admixed with a pipette, incubated for 2 min at room temperature and transferred to a Neubauer counting chamber. The number of cells was determined immediately after the incubation period in a reverse phase contrast microscope whereby the cells were counted within four large squares. In this process vital cells were not stained in contrast to avital cells. Weakly stained cells were considered to be avital.

The number of vital cells/ml was derived from the number of non-stained cells of the four large squares multiplied by the chamber factor of $10^4$ and the dilution factor of the cell suspension in the eosin solution.

Determination of the Cell Number by Electronic Counting in a Coulter Counter (Lindl and Bauer, 1989)

The measurement of the cell number in a Coulter counter is based on the cells flowing between two platinum electrodes. If a cell passes through the opening of the two electrodes then the resistance of the current flowing through the electrodes changes proportionally to the size of the cell. This generates a voltage impulse which is recorded and thus enables the cells to be quantified.

In order to determine the number of cells 25 µl of the cell suspension was transferred to 3 ml Iso-Osmol a carrier liquid for the Coulter counter and injected into the apparatus.

In this type of cell counting the total cell number of the cell suspension is determined. It is not possible to differentiate between vital and avital cells.

d. Detachment of Adherent Cells by Trypsin/EDTA

Adherent cells could be detached enzymatically from the bottom of the respective culture vessel by treatment with trypsin/EDTA. For this the culture supernatant was carefully decanted and the cells were washed twice with prewarmed (37° C.) culture medium. In order to detach the cells from the bottom of the culture vessel these were incubated for 5 min with a trypsin/EDTA solution (1×) at room temperature. The volume of trypsin/EDTA solution was selected in this case such that the bottom of the respective culture vessel was covered with 2–3 mm of the enzymatic solution. At the end of the incubation period the cells were detached from the bottom by carefully shaking the flask, removed from the culture vessel and admixed with an equal volume of RPMI 1640 complete medium I. Afterwards the cells were sedimented for 10 min at 1600 rpm in a Minifuge T. The supernatant was discarded, the cell sediment was resuspended in cold PBS and again centrifuged under the same conditions. The cells were then resuspended in culture medium or buffer depending on their further use.

e. Isolation of Mononuclear Cells From Human Blood

Isolation of Human PBL From Buffy Coat by Centrifugation in Isotonic Density Gradients (Böyum, 1968. Scand. J. Clin. Lab. Invest. 21 (Suppl 97), 77–89; Böyum 1976. Scand. J. Clin. Lab. Invest. 5 (Suppl. 5), 5–15)

In order to isolate human PBL the buffy coat of healthy donors was mixed and diluted with RPMI 1640 complete medium II in a volume ratio of 1:2. 20 ml cold lymphocyte separation medium was placed in polypropylene tubes (50 ml) and carefully covered with a layer of 15 ml of the diluted buffy coats. The fractionation was carried out by centrifugation for 30 min at room temperature and 1600 rpm (acceleration 4/brake 4) in a Minifuge T. The readily visible band between the sample and separation medium was isolated with the aid of a Combitip pipette. The collected fractions were sedimented for 10 min at room temperature and 1600 rpm to remove the separation medium. The supernatant was decanted and the cells were washed three times with RPMI 1640 complete medium II or cold PBS depending on their use.

Stimulation and Culture of Human PBL

After isolation of human PBL by means of centrifugation in isotonic density gradients it was possible to set up peripheral lymphocyte cultures. Normally blood cells die relatively rapidly in culture. However, lymphocytes can be kept in culture for several generations. In order to achieve a proliferation of these cells they were stimulated with the mitogen PHA-M, the lectin extract from the red scarlet runner (Phaseolus vulgaris).

For the stimulation the isolated cells were adjusted to a cell density of $1\times10^6$ cells/ml in RPMI 1640 complete medium II in tissue culture flasks (175 $cm^2$/800 ml) and incubated for 72 h at 37° C. and 5% $CO_2$. In order to avoid the cell density becoming too high, the cell suspension was diluted after 24 h with culture medium in a volume ratio of 1:1. After completion of the stimulation period the mitogen PHA-M was removed by washing three times with RPMI 1640 complete medium II. For the cell expansion the stimulated lymphocytes were adjusted to a cell density of $5-7\times10^6$ cells/ml in RPMI 1640 complete medium IV and cultured for 24 hours.

Preparation of Leucocyte-Rich Plasma from Whole Blood (Böyum, 1968)

Venous fresh blood from healthy donors was admixed with sterile 10% (w/v) EDTA solution in a volume ratio of 49:1 to prevent coagulation. In order to achieve a rapid mixing of these components small volumes of 8–9 ml blood were collected from the donor in polystyrene tubes (14 ml). In order to prepare leucocyte-rich plasma, EDTA-blood and dextran 75 were mixed in a volume ratio of 10:1. The two components were thoroughly mixed and the erythrocytes were sedimented for a period of 60 min at room temperature. Subsequently the almost clear supernatant, the leucocyte-rich plasma, was carefully removed and used to isolate monocytes.

Isolation of Human Monocytes from Leucocyte-rich Plasma by Centrifugation in a Hypertonic Density Gradient (Böyum, 1983, Scan. J. Clin. Lab. Invest. 17, 429–436)

It was possible to isolate non-stimulated monocytes from whole blood or leucocyte-rich plasma in a hypertonic solution. For this 3 ml of the hypertonic separation medium NycoPrep 1.068 was placed in polystyrene tubes (14 ml) and carefully covered with a layer of 6 ml leucocyte-rich plasma. The tubes were closed and centrifuged for 15 min and 600×g (acceleration 4/brake 4) in a Minifuge T. After centrifugation the clear plasma phase was removed and discarded up to 5 mm above the broad diffuse band. The remaining plasma phase and half of the broad diffuse band was removed and the cells were sedimented by centrifugation in a Minifuge T for 7 min under the same conditions. The cell sediment was subsequently resuspended and washed twice in 6 ml wash solution to remove residues of the separation medium.

| Nycoprep 1.068 | 13% (w/v) | Nycodenz |
|---|---|---|
| | 0.58% (w/v) | NaCl |
| | 5 (mM) | Tricine/NaOH pH 7.4 |
| | density | 1.068 ± 0.001 g/ml (20° C.) |
| | osmolarity | 335 ± 5 mOsm |

| Wash solution | 0.9% (w/v) | NaCl |
| --- | --- | --- |
| | 0.13% (w/v) | EDTA |
| | 1% (w/v) | BSA (fraction V) |

Isolation of Human Monocytes from Buffy Coat by Adherence (Andreesen et a., 1983, J. Immun. Methods 56, 295–304)

Mononuclear cells were isolated from the buffy coat by centrifugation in isotonic density gradients and washed three times with serum-free RPMI 1640 medium. In order to isolate the monocytes the cells were adjusted to a cell density of $5\times10^6$ cells/ml in tissue culture flasks (175 cm²/800 ml) containing 20 ml RPMI 1650 complete medium II and incubated for 45 min at 37° C. and 5% $CO_2$. Non-adherent cells were removed by decanting the medium after the incubation was completed. The cell layer at the bottom of the tissue culture flask was subsequently washed twice with pre-heated (37° C.) serum-free RPMI 1640 medium to remove residues of suspension cells. The cell layer was admixed with 30 ml RPMI 1640 complete medium V and incubated for a further 24 h under the same conditions. The adherent monocytes were detached by treatment with trypsin/EDTA.

EXAMPLE 12

Immunological Methods a. Flow Cytofluorometric Analysis of Cell Subpopulations from Human Blood by Direct and Sequential Antibody Staining For the flow cytofluorometric analysis the cells to be characterized were adjusted in FACS-PBS to a cell density of $1\times10^7$ cells/ml. The antibody stock solutions were diluted with FACS-PBS in a volume ratio of 1:50. For the direct and sequential antibody staining 50 µl of the cell suspension ($1\times10^7$ cells/ml) was placed in the wells of a microtitre plate with a conical bottom.

| Antibodies for the flow cytofluorometric analysis of mononuclear human blood cells | | | |
| --- | --- | --- | --- |
| Antibodies | Specificity | Fluorescent dye | Antibody staining |
| anti-Leu-12 (CD19) | Leu-12 (CD19) B lymphocytes | PE | direct |
| anti-Leu-5b (CD2) | Leu-5 (CD2) T lymphocytes | FITC | direct |
| anti-monocyte (CD14) | gp 55 monocytes macrophages | — | sequential |
| anti-leu-2a (CD8) | cytotoxic T lymphocytes | FITC | direct |
| anti-leu-3a (CD4) | helper T lymphocytes | PE | direct |

Subsequently the cell suspension was admixed with an equal volume of the antibody which in the case of a direct antibody staining is coupled to a fluorescent dye. The mixtures were incubated for 30 min at 4° C. and subsequently centrifuged at 1400 rpm and room temperature for 2 min in a Minifuge T to sediment the cells.

The supernatants were removed and the cell sediment was resuspended in 200 µl FACS-PBS and centrifuged again as described above to remove residues of non-bound antibody. The supernatant was removed and the cell sediment was resuspended in 100 µl FACS-PBS in the case of a direct antibody staining. In the case of the sequential antibody staining the cell sediment was taken up in 100 µl of a solution of the goat-anti mouse Ig-R-PE (3 µg/ml) antibody labelled with phycoerythrin after completion of the centrifugation of the cell sediment and incubated for 30 min at 4° C. Residues of the non-bound antibody were removed as described by washing with 200 µl FACS-PBS and the cell sediment was resuspended in 100 µl FAcS-PBS for the flow cytofluorometric cell analysis.

b. Determination of the Cell Vitality by Pronidium Iodide Staining in the Flow Cytofluorometric Analyzer The number of vital and avital cells can be determined by flow cytofluorometric analysis after staining the cells with the fluorescent dye propidium iodide. This dye is only taken up by avital cells. For this the cell suspension is adjusted in PBS to a concentration of $0.5–1\times10^6$ cells/ml. 180 µl is taken from this cell suspension and admixed with 20 µl of a propidium iodide solution (5 µg/ml). After an incubation period of 5 min 100 µl of the solution was injected into the cell analyzer. The percentage distribution of the vital and avital cells could be determined by a statistical analysis in the Lysis II program of the cell analyzer.

c. Quantitative Determination of AZT in Cell Extracts by Means of a $^{125}$I-AZT Radioimmunoassay A commercial $^{125}$I-AZT RIA test kit was used for the quantitative determination of AZT. Buffers and solutions were prepared according to the instructions of the manufacturer and used in the test kit. The reaction mixtures were pipetted according to the scheme (Tab.) shown below, carefully mixed and incubated for 2 h at room temperature. Subsequently 500 µl of the goat anti-rabbit antibody was added to precipitate the complex of $^{125}$I-AZT and the AZT antibody (from rabbits). The mixtures were mixed and incubated for a further 30 min at room temperature.

| Pipetting scheme of the $^{125}$I-AZT radioimmunoassay for the quantitative determination of AZT in cell extracts | | | | |
| --- | --- | --- | --- | --- |
| | non-binding standard | zero standard | standard | sample |
| zero standard [µl] | 300 | 200 | — | — |
| standard [µl] | — | — | 200 | — |
| sample [µl] | — | — | — | 200 |
| $^{125}$I-AZT [µl] | 100 | 100 | 100 | 100 |
| AZT antibody [µl] | — | 100 | 100 | 100 |

The mixtures were subsequently centrifuged at 1000×g for 20 min to sediment the precipitation complex. After decanting the supernatant the radioactivity of the sediment was measured for 60 sec in a liquid scintillation analyzer. In order to determine the absolute value, the radioactivity of 100 µl $^{125}$I-AZT was determined under the same conditions after an incubation of 2 h at room temperature. The concentrations of AZT in the biological matrix were determined with the aid of a calibration curve which was established with standards from the test kit with a defined substance concentration.

EXAMPLE 13

Characterization of the Intracellular Enzymatic Cleavage of BM 21.1290 Na

The results of the in vitro pharmakokinetic studies with AZT-DMDOPE and AZT in stimulated and non-stimulated human PBL as well as in thymidine kinase deficient P3X63Ag8.653 cells indicate an intracellular enzymatic cleavage of AZT-DMDOPE with a direct release of AZT-MP and of the corresponding thioether lipid moeity DMDOP. It is intended to verify this intracellular enzymatic cleavage demonstrated in further experiments at a subcellular level by a direct detection of the corresponding metabolites. Hence for an unequivocal characterization of the cleavage it was necessary to identify the previously known metabolites which can be formed from the parent substance AZT-DMDOPE. These include the substances DMDOP, AZT and AZT-MP as well as substances which are formed by oxidation of the sulphur in the thioether lipid moiety of the parent substance AZT-DMDOPE.

a. Development of Methods for the Determination of the $R_f$ Values of AZT-DMDOPE and its Potential Metabolites It was possible to identify the potential metabolites of AZT-DMDOPE with the aid of TLC. For this the non-radioactively labelled pure substances were analysed with the aid of various separation systems and subsequently the Rf values were determined.

For this the substances were dissolved at a concentration of 4 mg/ml in a mixture of ethyl acetate and methanol (1:1, v/v). 5 µl of these solutions was transferred with the aid of a microcapillary to the stationary phase and analysed.

Thioether lipids such as AZT-DMDOPE, DMDOP as well as those which are formed by oxidation of the sulphur could be labelled with the aid of a reagent containing iodine which stains the thioether lipid moiety of these compounds. AZT and AZT-MP could only be made visible on the TLC plates with a fluorescence indicator on the basis of their absorbance in the ultraviolet range at 254 nm. AZT-DMDOPE, the substance with a thioether lipid moiety and a chromophoric group could be detected with both types of detection.

Three separation systems were established for the thin layer chromatographic analysis of the substances which differed with regard to their stationary and mobile phases.

In the first separation system, the IBA system, using silica gel 60 as the stationary phase the parent substance AZT-DMDOPE could be identified in addition to DMDOP. A mixture of 2-propanol:n-butyl acetate:redistilled water (10:6:4 v/v/v) was used as the mobile phase.

This separation system was developed further by using 2-propanol:n-butyl acetate redistilled water:glacial acetic acid (3:5:1:1, v/v/v/v) as the mobile phase (IBAE system). The substances AZT-DMDOPE and DMDOP could be separated in this case on silica gel 60 TLC plates as described for the IBA separation system. In addition AZT and AZT-MP could be separated with a fluorescence indicator in UV light at 254 nm and using a stationary phase of silica gel 60. Due to the AZT moiety it was also possible to detect the parent substance AZT-DMDOPE as well as its oxidation products.

After the substances were visualized on the TLC plate the $R_f$ values were determined.

A further separation system was available to differentiate the substance AZT-DMDOPE from DMDOP. For this a mixture of n-heptane and ethyl acetate (4:1, v/v) was used as the mobile phase and silica gel 60 as the stationary phase. The detection was carried out with the reagent containing iodine already described above by staining the thioether lipid moiety of the substances.

In comparison to the IBA and IBAE system a considerably lower $R_f$ value was determined for the substance DMDOP with this separation system. The reason for this is a unpolar mobile phase compared to the IBA and IBAE system consisting of n-heptane and ethyl acetate. The detection limit of the substances after thin layer chromatographic analysis and detection with an iodine-containing reagent- was determined to be 0.1 µg in all separation systems.

In summary it can be stated that with the aid of the described thin layer chromatographic separation systems it is possible to unequivocally characterize all substances via their $R_f$ values which come into consideration according to the present state of knowledge as potential metabolites of AZT-DMDOPE.

TABLE $R_f$ values of AZT-DMDOPE and DMDOP after separation in the IBA system (2-propanol:n-butyl acetate:redistilled water, 10:6:4, v/v/v) with silica gel 60 as the stationary phase (means ± SD, n = 6 determinations)

| Test substance | $R_f$ value |
| --- | --- |
| AZT-DMDOPE | 0.68 ± 5.2 × 10$^{-3}$ |
| DMDOP | 0.93 ± 0.00 |

TABLE $R_f$ values of AZT-DMDOPE, DMDOP, AZT and AZT-MP after separation in the IBAE system (2-propanol:n-butyl acetate:redistilled water:glacial acetic acid, 3:5:1:1, v/v/v/v) with silica gel 60 and 60 F 254 as the stationary phase (means ± SD, n = 6 determinations)

| Test substance | $R_f$ value |
| --- | --- |
| AZT-DMDOPE | 0.57 ± 1 × 10$^{-3}$ |
| DMDOP | 0.99 ± 0.00 |
| AZT | 0.85 ± 0.00 |
| AZT-MP | 0.14 ± 0.00 | b. Enzymatic Cleavage of AZT-DMDOPE by Cell Homogenates of Stimulated and Non-stimulated Human PBL and CEM-SS Cells The cleavage of AZT-DMDOPE was examined with the aid of an enzyme assay using [$^{14}$C]-AZT-DMDOPE and AZT-DMDOPE as the substrate. Firstly cell homogenates of CEM-SS cells and human PBL were used as the enzyme source.

TABLE $R_f$ values of AZT-DMDOPE and DMDOP after thin layer chromatographic separation in the HE system (n-heptane:ethyl acetate, 4:1, v/v) with silica gel 60 as the stationary phase (means ± SD, n = 6 determinations)

| Test substance | $R_f$ value |
| --- | --- |
| AZT-DMDOPE | 0.0 ± 0.00 |
| DMDOP | 0.36 ± 0.00 |

The latter were homogenized directly after their isolation after stimulation with PHA-M as well as in the non-stimulated state and used in the enzyme assay.

In order to prepare the cell homogenates, cell suspensions were mechanically disrupted in a glass homogenizer at a density of $5 \times 10^7$ cells/ml 50 mM Tris (pH 7.4) The cell disruption in this case was optically monitored in a reverse phase contrast microscope.

TABLE $R_f$ values of the substances 1–4 (FIG. 18) after 1, 3, 6 and 24 h incubation and enzymatic cleavage of [$^{14}$C]-AZT-DMDOPE by cell homogenates of $5 \times 10^7$ stimulated and non-stimulated human PBL and CEM-SS cells. Separation in the IBA/IBAE system with silica gel 60 as the stationary phase (means ± SD, n = 4 determinations)

|  | $R_f$ value Substance 1 | $R_f$ value Substance 2 | $R_f$ value Substance 3 | $R_f$ value Substance 4 |
|---|---|---|---|---|
| CEM-SS | $0.41 \pm 2.5 \times 10^{-2}$ | $0.56 \pm 2.5 \times 10^{-2}$ | $0.86 \pm 5.8 \times 10^{-3}$ | $0.96 \pm 0.0$ |
| stimulated human PBL | — | $0.65 \pm 9.5 \times 10^{-3}$ | $0.86 \pm 5.8 \times 10^{-3}$ | $0.94 \pm 0.0$ |
| non-stimulated human PBL | — | $0.65 \pm 1.7 \times 10^{-2}$ | — | $0.92 \pm 1.2 \times 10^{-2}$ |

Firstly 1 ml of this cell homogenate was used in the enzyme assay without prior determination of the protein concentration. 0.98 nmol [$^{14}$C]-AZT-DMDOPE (1.67 kBq) was used as the substrate.

In order to ensure a substrate saturation a further 50 nmol of the non-radioactively labelled compound was added. [$^{14}$C]-AZT-DMDOPE carries the radioactive label in the thioether lipid moiety and thus enables an unequivocal identification of the potential metabolite [$^{14}$C]-DMDOP.

The mixtures were incubated for 1, 3, 6 and 24 h in a water bath at 37° C. A mixture without addition of cell homogenate was also carried out as a reference. Subsequently the cleavage products were extracted with diethyl ether:2-propanol (9:1, v/v) and analysed by thin layer chromatography in the IBA and IBAE system (FIG. 18). After the substances were separated the TLC plate was measured for 15 min in a radio TLC analyzer to detect the radioactively labelled substances. It was finally possible to unequivocally identify the metabolites by determining the $R_f$ values.

TABLE $R_f$ values of the substances 1 and 2 (FIG. 18) after 1, 3, 6 and 24 h incubation of [$^{14}$C]-BM 21.1290 Na. Separation in the IBA/IBAE system with silica gel 60 as the stationary phase (means ± SD, n = 4 determinations)

|  | $R_f$ value Substance 1 | $R_f$ value Substance 2 |
|---|---|---|
| CEM-SS | $0.41 \pm 5.7 \times 10^{-3}$ | $0.56 \pm 5.8 \times 10^{-3}$ |
| stimulated human PBL | — | $0.65 \pm 9.6 \times 10^{-3}$ |
| non-stimulated human PBL | — | $0.65 \pm 1.9 \times 10^{-3}$ |

The thin layer chromatographic analysis of the enzymatic cleavage products of AZT-DMDOPE by cell homogenates of stimulated and non-stimulated human PBL was carried out by using the IBA separation system. In the subsequent experiments with the CEM-SS cell homogenate the analysis of the cleavage products was carried out in the IBAE separation system. Since the $R_f$ values of the pure substances have been determined for both separation systems it was possible to directly compare the results to identify the substances after enzymatic cleavage of AZT-DMDOPE.

After enzymatic cleavage of [$^{14}$C]-AZT-DMDOPE by cell homogenates of stimulated and non-stimulated human PBL three unknown substances were detected in the TLC chromatogram. With Rf values of $0.65 \pm 9.5 \times 10^{-2}$ (n=4) and $0.65 \pm 1.7 \times 10^{-2}$ (n=4) for stimulated and non-stimulated human PBL the substance peak 2 could be unequivocally assigned to the parent substance [$^{14}$C]-AZT-DMDOPE. The $R_f$ values of substance peak 4 of $0.94 \pm 0.00$ (n=4) and $0.92 \pm 1.2 \times 10^{-2}$ (n=4) were identical to the values of DMDOP which were determined by TLC analysis of the pure substances. Substance peak 3 having an Rf value of $0.86 \pm 5.8 \times 10^{-3}$ (n=4) could not be allocated to any of the known substances. The results were confirmed by analysis of the enzymatic cleavage of [$^{14}$C]-AZT-DMDOPE by CEM-SS cell homogenates. Substance peaks 2 and 4 having $R_f$ values of $0.56 \pm 2.5 \times 10^{-2}$ (n=4) and $0.96 \pm 0.00$ (n=4) could be unequivocally identified as AZT-DMDOPE and DMDOP respectively whereas substance peak 1 having an $R_f$ value of $0.41 \pm 2.5 \times 10^{-2}$ (n=4) could be assigned to an oxidation product. It was not possible to assign substance peak 3 even in the IBAE system after comparison of the $R_f$ values (FIG. 18). Furthermore it was possible to show that after incubation of [$^{14}$C]-AZT-DMDOPE only the parent substance was detected when the cell homogenate was not added (FIG. 18).

The thin layer chromatographic analysis of the reaction mixtures therefore proves that the substance DMDOP is released from the parent substance.

EXAMPLE 14

9-(β-D-Arabinofuranosyl)-2-fluoroadenine-5-phosphoric Acid-(3-dodecylmercapto-2-decyloxy)-propyl Ester (Fludarabine Conjugate)

34.8 g (0.07 mol) phosphoric acid (3-dodecylmercapto-2-decyloxy)-propyl ester was dissolved in 130 ml absolute pyridine, admixed with 15 g methanesulfonic acid chloride under nitrogen and stirred for 3 hours at room temperature.

Then 20 g fludarabine was carefully added and the solution was stirred for a further 48 hours at room temperature. Fludarabine was synthesized analogously to J. Heterocyclic Chem. 16, 157 (1979).

After hydrolysis of the reaction mixture by adding 30 ml 1 M triethylammonium bicarbonate solution and stirring for 1 hour, the pyridine was removed in a vacuum and the residue was partitioned between 200 ml t-butylmethyl ether (MTB) and 150 ml water, the organic phase was separated and evaporated in a rotary evaporator.

The residue was purified chromatographically on RP-18 with methanol/0.02 M acetate buffer pH 4 8/2 as the eluant.

The fractions containing product were concentrated down to the water portion, extracted with MTB and the MTB phase was adjusted with sodium methylate solution against Friscolyt to pH 7.

After the solvent was removed by evaporation the residue was suspended in acetone, the amorphous precipitate was suction filtered and dried.

Yield: 23.7 g (43%). Amorph. Rf=0.45 (TLC-mobile solvent: isopropanol/butyl acetate/water/ammonia 50/30/15/5).

EXAMPLE 15

2-Chloro-2'-deoxyadenosine-5'-phosphoric Acid-(3-dode-cylmercapto-2-decylox)-propyl Ester (Cladribine Conjugate)

The cladribine conjugate was prepared in a 35% yield analogously to example 14 using 4.2 g phosphoric acid-(3-dodecylmercapto-2-decyloxy)-propyl ester, 3 g methanesulfonic acid, 100 ml pyridine and 2 g cladribine. $R_f$=0.41 (mobile solvent as in example 14). Cladribine was prepared analogously to J. Am. Chem. Soc. 106, 6379 (1984).

EXAMPLE 16

[3-(2-Deoxy-β-D-erythro-pentofuranosyl)-3,6,7,8tetrahydroimidazo[4,5-d][1,3]diazepin-8-ol]-5'-phosporic acid-(3-dodecylmercapto-2-decyloxyl-proyl ester (pentostatin conjugate)

The pentostatin conjugate was prepared in a 27% yield analogously to example 14 using 4.2 g phosphoric acid-(3-dodecylmercapto-2-decyloxy)-propyl ester, 3 g methanesulfonic acid, 100 ml pyridine and 2.1 g pentostatin. $R_f$=0.52 (mobile solvent as in example 14). Pentostatin was prepared analogously to J. Org. Chem. 47, 3457 (1982) and J. Am. Chem. Soc. 101, 6127 (1979).

The invention claimed is:

1. A method of determining if a compound is a substrate of an isolated membranous lipid cleavage enzyme complex (LCE), which LCE cleaves a conjugate of the type L-B-D in which:

L represents a lipid-like residue, B represents a phosphate bridge or a thiophosphate bridge and D denotes a pharmacologically active substance; or B-D represents a pharmacologically active substance phosphonate and the LCE induces a cleavage of a covalent bond between the lipid moiety L and the residue -B-D;

and wherein said LCE has a molecular weight of about 120,000 to about 160,000, as determined by the SDS-PAGE method, is free of phospholipase C activity, is activated by D609 (Tricyclodecan-9-yl-xanthogenat) and is inhibited by $Ca^{2+}$, $Zn^{2+}$ or $Mn^{2+}$, said method comprising:

a) obtaining the LCE by:
      i) preparing a homogenate of cells selected from the group consisting of leukocytes, monocytes, tumour cells, kidney cells, lymphocytes, cells of the immuno/lymphatic system, and/or macrophages;
      ii) isolating plasma membranes from the cell homogenate; and
      iii) identifying LCE cleavage activity in a fraction of the isolated plasma membranes, whereby LCE cleavage activity indicates presence of LCE in the fraction;
   b) incubating the LCE with the compound; and
   c) detecting cleavage products, wherein the presence of cleavage products indicates that the compound is a substrate or a ligand of the LCE.

2. The method of claim 1, wherein the LCE is present in a subcellular system.

3. A method of determining if a compound is an activator or an inhibitor of an isolated mebranous lipid cleavage enzyme complex (LCE), which LCE cleaves a conjugate of the type L-B-D in which:

L represents a lipid-like residue, B represents a phosphate bridge or a thiophosphate bridge and D denotes a pharmacologically active substance; or B-D represents a pharmacologically active substance phosphonate and the LCE induces a cleavage of a covalent bond between the lipid moiety L and the residue -B-D;

and wherein said LCE has a molecular weight of about 120,000 to about 160,000, as determined by the SDS-PAGE method, is free of phospholipase C activity, is activated by D609 (Tricyclodecan-9-yl-xanthogenat) and is inhibited by $Ca^{2+}$, $Zn^{2+}$ or $Mn^{2+}$, said method comprising:

a) obtaining the LCE by:
      preparing a homogenate of cells selected from the group consisting of leukocytes, monocytes, tumour cells, kidney cells, lymphocytes, cells of the immuno/lymphatic system, and/or macrophages;
      ii) isolating plasma membranes from the cell homogenate; and
      iii) identifying LCE cleavage activity in a fraction of the isolated plasma membranes, whereby LCE cleavage activity indicates presence of LCE in the fraction;
   b) incubating the LCE with the compound;
   c) adding a substrate or ligand of the LCE;
   d) detecting a change in enzymatic activity, wherein a change in enzymatic activity indicates that the compound is an activator or an inhibitor of the LCE.

4. The method of claim 3, wherein the LCE is present in a subcellular system.

5. A method of obtaining an isolated membranous lipid cleavage enzyme complex (LCE), which cleaves a conjugate of the type L-B-D in which:

L represents a lipid-like residue, B represents a phosphate bridge or a thiophosphate bridge and D denotes a pharmacologically active substance; or B-D represents a pharmacologically active substance phosphonate and the LCE induces a cleavage of a covalent bond between the lipid moiety L and the residue -B-D;

and wherein said LCE has a molecular weight of about 120,000 to about 160,000, as determined by the SDS-PAGE method, is free of phospholipase C activity, is activated by D609 (Tricyclodecan-9-yl-xanthogenat) and is inhibited by $Ca^{2+}$, $Zn^{2+}$ or $Mn^{2+}$, the method comprising:

preparing a homogenate of cells selected from the group consisting of leukocytes, monocytes, tumour cells, kidney cells, lymphocytes, cells of the immuno/lymphatic system, and/or macrophages;
   ii) isolating plasma membranes from the cell homogenate; and
   iii) identifying LCE cleavage activity in a fraction of the isolated plasma membranes, whereby LCE cleavage activity indicates presence of LCE in the fraction.

6. The method of claim 5, wherein the identifying LCE cleavage activity comprises contacting the fraction with AZT-DMDOPE and determining the presence or absence of AZT-MP or DMDOP, wherein the presence of AZT-MP or DMDOP indicates the presence of LCE in the fraction.

7. The method of claim 5, wherein the cells are leukocytes.

8. The method of claim 7, wherein the leukocytes are human peripheral blood leukocytes.

9. The method of claim 5 wherein the identifying LCE cleavage activity comprises contacting the fraction with FLT-DMDOPE and determining the presence or absence of FLT-MP or DMDOP, wherein the presence of FLT-MP or DMDOP indicates the presence of LCE in the fraction.

10. The method of claim 9, wherein the cells are leukocytes.

11. The method of claim 10, wherein the leukocytes are human peripheral blood leukocytes.

12. The method of claim 5 wherein the identifying LCE cleavage activity comprises contacting the fraction with 5-FU-DMDOPE and determining the presence or absence of 5-FU-MP or DMDOP, wherein the presence of 5-FU-MP or DMDOP indicates the presence of LCE in the fraction.

13. The method of claim 12, wherein the cells are leukocytes.

14. The method of claim 13, wherein the leukocytes are human peripheral blood leukocytes.

15. The method of claim 1, wherein the substrate comprises a glyceryl ether of AZT-MP.

16. The method of claim 1, wherein the substrate comprises a glyceryl ether of a nucleoside monophosphate.

* * * * *